US007060271B2

(12) United States Patent
Ramakrishnan et al.

(10) Patent No.: US 7,060,271 B2
(45) Date of Patent: Jun. 13, 2006

(54) INHIBITORY IMMUNOGLOBULIN POLYPEPTIDES TO HUMAN PDGF BETA RECEPTOR

(75) Inventors: Vanitha Ramakrishnan, Belmont, CA (US); Maria Amelia Escobedo, San Francisco, CA (US); Larry J. Fretto, Belmont, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 1077 days.

(21) Appl. No.: 09/003,810

(22) Filed: Jan. 7, 1998

(65) Prior Publication Data

US 2003/0059425 A1 Mar. 27, 2003

Related U.S. Application Data

(63) Continuation of application No. 08/258,283, filed on Jun. 10, 1994, now Pat. No. 5,817,310, which is a continuation-in-part of application No. 08/253,440, filed on Jun. 7, 1994, now abandoned, which is a continuation of application No. 07/801,795, filed on Dec. 2, 1991, now abandoned.

(51) Int. Cl.
*A61K 39/395* (2006.01)
*C07K 16/28* (2006.01)
(52) U.S. Cl. .............................. 424/143.1; 424/130.1; 424/133.1; 424/141.1; 424/152.1; 424/172.1; 530/387.1; 530/387.3; 530/388.1; 530/388.2; 530/388.22
(58) Field of Classification Search ............. 424/130.1, 424/133.1, 141.1, 172.1; 530/387.1, 388.2
See application file for complete search history.

(56) References Cited

U.S. PATENT DOCUMENTS 5,268,358 A 12/1993 Fretto
5,468,468 A 11/1995 La Rochelle et al.
5,817,310 A * 10/1998 Ramakrishnan et al. . 424/143.1

FOREIGN PATENT DOCUMENTS

| EP | 327 369 | 2/1989 |
| WO | WO 90/07861 | 7/1990 |
| WO | WO 90/10013 | 9/1990 |
| WO | WO 92/13867 | 8/1992 |
| WO | WO 93/10805 | 6/1993 |
| WO | WO 93/11223 | 6/1993 |

OTHER PUBLICATIONS

Matsui et al., Isolation of novel receptor cDNA establishes the existence of two PDGF receptor genes, *Science* (1989) 243:800-804.
Vasbotn et al., A monoclonal antibody against PDGF B-chain inhibits PDGF-induced DNA synthesis in C3H fibroblasts and prevents binding of PDGF to its receptor, *Biochem. Biophys. Acta* (1990) 1054:246-249.
Yarden et al. , Structure of the receptor for platelet-derived growth factor helps define a family of closely related growth factor receptors, *Nature* (1986) 323:226-232.
Antoniades et al., Malignant epithelial cells in primary human lung carcinomas coexpress in vivo platelet-derived growth factor (PDGF) and PDGF receptor mRNAs and their protein products (1992), *Proc. Natl. Acad. Sci. USA* 89:3942-3946.
Bellot et al., High-Affinity Epidermal Growth Factor Binding is Specifically Reduced by a Monoclonal Antibody and Appears Necessary for Early Responses (1990), *J. Cell Biol.* 110:491-502.
Bishayee et al., Characterization of a Novel Anti-Peptide Antibody that Recognizes a Specific Conformation of the Platelet-Derived Growth Factor Receptor (1988), *Mol. Cell. Biol.* 8:3696-3702.
Claesson-Welsh et al., Identification and Structural Analysis of the A Type Receptor for Platelet-Derived Growth Factor (1989), *J. Biol. Chem.* 264:1742-1747.
Claesson-Welsh et al., cDNA cloning and expression of the human A-type platelet-derived growth factor (PDGF) receptor estabilshes structural similarity to the B-type PDGF receptor (1989), *Proc. Natl. Acad. Sci. USA* 86:4917-4921.
Cunningham, Antibody Engineering—How to by Human (1992), *Trends Biotechnol.* 10:10-11.
Daniel et al., Biosynthetic and Glycosylation Studies of Cell Surface Platelet-Derived Growth Factor Receptors (1987), *J. Biol. Chem.* 161:9778-9784.
Dermer, Human cancer research (1983) *Science* 221:318.
Dillman et al., Intensive chemotherapy with autologous peripheral-blood stem-cell rescue in metastatic breat cancer (1994), *J. Clin. Oncol.* 12:2237.
Divgi et al., Phase I and imaging trial of indium 111-labeled anti-epidermal growth factor receptor monoclonal antibody 225 in patients with squamous cell lung carcinoma (1991), *J. Natl. Cancer Inst.* 83:97-104.

(Continued)

*Primary Examiner*—Phillip Gambel
(74) *Attorney, Agent, or Firm*—Morgan, Lewis & Bockius LLP

(57) ABSTRACT

The present invention is directed towards immunoglobulin polypeptides that specifically bind to the extracellular domain of the human type beta PDGF receptor. The binding of the immunoglobulin polypeptides to the receptor inhibits PDGF-induced (or stimulated) receptor activation as indicated by inhibition of receptor phosphorylation and dimerization, and by inhibition of PDGF-mediated mitogenesis, chemotaxis and migration of cells displaying the human PDGF type beta receptor on the cell surface. Nucleic acids encoding the immunoglobulin polypeptides are also included in the invention. The immunoglobulin polypeptides have diagnostic and therapeutic uses.

19 Claims, 11 Drawing Sheets

OTHER PUBLICATIONS

Ennis et al., Anti-Epidermal Growth Factor Receptor Antibodies Inhibit the Autocrine-Stimulated Growth of MDA-468 Human Breast Cancer Cells (1989), *Mol. Endocrinol.* 3:1830-1838.

Eppstein et al., Inhibition of Epidermal Growth Factor/Transforming Growth Factor-α-Stimulated Cell Growth by a Synthetic Peptide (1989), *J. Cell. Physiol.* 141:420-430.

Escobedo et al., Platelet-Derived Growth Factor Receptors Expressed by cDNA Transfection Couple to a Diverse Group of Cellular Responses Associated with Cell Proliferation (1988), *J. Biol. Chem.* 263:1482-1487.

Fendly et al., Characterization of murine monoclonal antibodies reactive to either the human epidermal growth factor receptor or HER2/neu gene product (1990), *Cancer Res.* 50:1550-1558.

Ferns et al., Inhibition of Neointimal Smooth Muscle Accumulation After Angioplasty by an Antibody to PDGF (1991), *Science* 253:1129-1132.

Harris et al., Therapeutic Antibodies—the Coming of Age (1993), *Trends Biotechnol.* 11:42-44.

Hart et al., Synthesis, Phosphorylation, and Degradation of Multiple Forms of the Platelet-Derived Growth Factor Receptor Studied Using a Monoclonal Antibody (1987), *J. Biol. Chem.* 262:107870-10785.

Heidaran et al., Chimeric α- and Bβ-Platelet-Derived Growth Factor (PDGF) Receptors Define Three Immunoglubulin-Like Domains of the α-PDGF Receptor that Determine PDGF-AA Binding Specificity (1990), *J. Biol. Chem.* 265:18741-18744.

Heldin et al., Binding of Different Dimeric Forms of PDGF to Human Fibroblasts: Evidence for Two Separate Receptor Types (1988), *EMBO J.* 7:1387-1393.

Kanakaraj et al., Ligand-Induced Interaction Between α- and β-Type Platelet-Derived Growth Factor (PDGF) Receptors: Role of Receptor Hererodimers in Kinase Activation (1991), *Biochemistry* 30:1761-1767.

Kawahara et al., Monoclonal Antibody C3.1 is a Platelet-Dervied Growth Factor (PDGF) Antagonist (1987), *Biochem. Biophys. Res. Commun.* 147:839-845.

Kawamoto et al., Monoclonal Antibodies to Epidermal Growth Reactor Receptors in Studies of Receptor Structure and Function (1990), *Cytotechnology* 3:279-293.

Kazlauskas et al., Phosphorylation of the PDGF Receptor β Subunit Creates a Tight Binding Site for Phosphatidylinositol 3 Kinase (1990), *EMBO J.* 9:3279-3286.

Keating et al., Processing of the Platelet-Derived Growth Factor Receptor (1987), *J. Biol. Chem.* 262:7932-7937.

Kovacs, Fibrogenic cytokines: the role of immune mediators in the development of scar tissue (1991), *Immunol. Today* 12:17-23.

Krane et al., Increased Dermal Expression of Platelet-Derived Growth Factor Receptors in Growth-Activated Skin Wound and Psoriasis (1991), *J. Invest. Dermatol.* 96:983-986.

Kumjian et al., Platelet-Derived Growth Factor (PDGF) Binding Promotes Physical Association of PDGF Receptor with Phospholipase C (1989), *Proc. Natl. Acad. Sci. USA* 86:8232-8236.

LaRochelle et al., Inhibition of platelet-derived growth factor autocrine growth stimulation by monoclonal antibody to the human alpha platelet-derived growth factor receptor (1993), *Cell Growth Differ.* 4:547-553.

Lerner et al., Monoclonal Antibody YB5.B8 Identifies the Human C-Kit Protein Product (1991), *Blood* 77:1876-1883.

Meyer-Ingold, Wound therapy: growth factors as agents to promote healing (1993), *Trends Biotechnol.* 11:3887-392.

Nilsson et al., Demonstration of stimulatory effects of platelet-derived growth factor on cultivated rat arterial smooth muscle cells. Differences between cells from young and adult animals (1983), *Exp. Cell. Res.* 145:231-237.

Osband et al., Problems in the investigational study and clinical use of cancer immunotherapy (1990), *Immunol. Today* 11:193-195.

Palman et al., Platelet-derived growth factor receptor (beta-subunit) immunoreactivity in soft tissue tumors (1992), *Lab. Invest.* 66:108-115.

Pascuale et al., A Distinctive Family of Embryonic Protein-Tyrosine Kinase Receptors (1990), *Proc. Natl. Acad. Sci. USA* 87:5812-5816.

Pellegrini et al., Characterization of a monoclonal antibody directed against the epidermal growth factor receptor binding site (1991), *Cancer Immunol. Immunother.* 34:37-42.

Plate et al., Platelet-derived growth factor receptor-beta is induced during tumor development and upregulated during tumor progression in endothelial cells in human gliomas (1992), *Lab. Invest.* 67:529-534.

Queen et al., A Humanized Antibody that Binds to the Interleukin 2 Receptor (1989), *Proc. Natl. Acad. Sci. USA*, 86:10029-10033.

Ramakrishnan et al., A Novel Monoclonal Antibody Dependent on Domain 5 of the Platelet-Derived Growth Factor Beta Receptor Inhibits Ligand Binding and Receptor Activation (1993), *Growth Factors* 8:253-265.

Reilly et al., Monoclonal Antibodies Directed Against Basic Fibroblast Growth Factor Which Inhibit Its Biological Activity In Vitro and In Vivo (1989), *Biochem. Biophys. Res. Commun.* 164:736-743.

Ronnstrand et al., Purification of the Receptor for Platelet-Derived Growth Factor from Porcine Uterus (1987), *J. Biol. Chem.* 262:2929-2932.

Ronnstrand et al., Characterization of Two Monoclonal Antibodies Reactive with the External Domain of the Platelet-Derived Growth Factor Receptor (1988), *J. Biol. Chem.* 263:10429-10435.

Seifert et al., Two Different Subunits Associate to Create Isoform-Specific Platelet-Derived Growth Factor Receptors (1989), *J. Biol. Chem.* 264:8771-8778.

Smits et al., Expression of platelet-derived growth factor and its receptors in proliferative disorders of fibroblastic origin (1992), *Am. J. Pathol.* 140, 639-648 Abstract Only.

Waldmann, Monoclonal Antibodies in Diagnosis and Therapy (1991), *Science*, 252:1657-1662.

Westermark et al., Platelet-derived growth factor in human glioma (1995), *Glia* 15:257-263.

Westermark et al., B-Type Receptor For Platelet-Derived Growth Factor Mediates a Chemotactic Response by Means of Ligand-Induced Activation of the Receptor Protein-Tyrosine Kinase (1990), *Proc. Natl. Acad. Sci. USA* 87:128-132.

Williams, Signal Transduction by the Platelet-Derived Growth Factor Receptor (1992), *Science*, 243:1564-1570.

* cited by examiner

SEQUENCE LISTING

<160> NUMBER OF SEQ ID NOS: 10

<210> SEQ ID NO 1
<211> LENGTH: 5
<212> TYPE: DNA
<213> ORGANISM: Homo sapiens

<400> SEQUENCE: 1 aagat                                                                    5

<210> SEQ ID NO 2
<211> LENGTH: 6
<212> TYPE: DNA
<213> ORGANISM: Homo sapiens

<400> SEQUENCE: 2 aaggat                                                                   6

<210> SEQ ID NO 3
<211> LENGTH: 4438
<212> TYPE: DNA
<213> ORGANISM: Homo sapiens -continued

```
<400> SEQUENCE: 3
cctcacatat ttcaaatcca tctcaaattc acattcacag atgtaagagc tgggaaagga         60
cggttttgac agggctgaac tgagctatgg tatgagtagc actcatcccc agaaagtctc        120
ttggtttgaa tttccgggaa aaggagctat agctgcaaaa atctgtttca caaatgtgct        180
aactataagc attttccaca gtgtttaata aaccatgcag ataagaaaat attattgaca        240
aacaaattaa taaaatgctc aaaataatct gatactaaat gcttgtagca tggcatgcaa        300
atcaccaaaa ataaatgtgc tatgcttcat ataaaatctc cagtaaggct gggtgtggtg        360
gctcacacct ataatcccaa cactctggga ggccgaggtg agagaactgc ttgaggccag        420
gagtttgaga ctagcctggc caacatagtg agacctcatc tctacaaaaa atcttaaaaa        480
tcagtgggac atggtggtgc acatctgtag ttctagctac ttgggagtct gaggcaggaa        540
gattgcttaa gcccaagagt ttgaggtccc tacactccag cctaagcgac agagggagac        600
cttgtctcta aataaataaa ttagttaatt gaatgtccag tcagttgata tatccaaatt        660
cttcccatgg taattttaaa aactttagtc ttaggagagt aaaagtcatg acataagac         720 ttcttataaa caactcagcc taatgagaaa tagaccctgt attttaagtgt catttaagta      780 tctatttctt cattgatcta ttcatttatt aactcctgta acaatcattt gcagacacct        840
actatgttga ggtagtataa actataaatt caacaagttt gataagggaa ataagagaga        900
ttgagtgaca gcttgaaggg gaggattctt tcaggcctgt gggaccgggt ggtggcatgg        960
agacattatt gtggacttga gggagttaat gtgacagtcc tcgtgtctcc agacactttc       1020
tctctgttag ggaagcaaga tttctatccc cagagtatgt atgtgttatg tctggactgc       1080
agtggcacag aactgtgttc aacgagtgac taccgctctg ctgtgtgccc tgggacttgg       1140
ggttaattga tcaatcattt ctatccagaa ggtaaccatg aggactgacg gaaccagtgt       1200
gtaccaagtg tctgttaagt gtctggtcaa tggttatcca taaagctact gcatggccat       1260
atgtaggaag aatacacacc gtgagcaaat ttttcccacg tgtaactctc acaacaaaat       1320
agcattaaat acttaatgtt tctggctaaa gaccatttca agacttgcag acaaaaaaa        1380 tagaaaaaat atctgacact caaatggagt tacaaaatta aaacggctga attccccagc       1440
ataaaaaaat atgaagcaag attgaaattt caagactaag tttaatatgg aaaaatacaa       1500
atatgtttga ggcctttcac agagcagcca gcatgaagca accaagaaaa ccacggaaat       1560
aatctggctg cctggaaata gtccggagtc agctgacaca gccacacgag agccctctta       1620
tgcttgtcat aagggtaaa ggaataattt cagaaaatta catttaaaag agaattatgg        1680
gggaagaaga tgctcccaga ggaaacaaat agtatggatg tgaagagcaa atacaacttt       1740
aacatgtttt gaacttcttg gaaactatgc taagtttagg cattgctagg atttggtatg       1800
atttaatccc cagctttctg ttctaaattt ttgttttctt ttttactctc aaataaatca       1860
tatgctagca ccagctgcaa agttacatat gttgtattag acgatcttcc atgaatacct       1920
aactggaaat tccaagattc agggccatgt gaatctaggc tggctgctta accaaaactt       1980
aatttaattt ttttcgttta ttttaggaaa aaaaattaac gaaagatgt ttcaagcaac        2040 cagtttccaa tccacgtcag caactatgac atttaatgaa acactgtgag catttagcat       2100
gagagctctg gactcagatg cagggagctt tgctagagaa gggaggaaaa agcaggcatg       2160
atgtggcggg ttgtggggga ctccaaggct ctatttccaa cttccatcag agaacttctg       2220
ttttcacctg gttttcaaat ttgctttcca aagggattt gtttaagta aaggatacag         2280 aggtttataa aagtttgaaa acttctacat tgcaggatgt gcaggctctt gccagatggg       2340
```

```
acagtgtatg agactcttcc agggtgacgt cttaggcaat ttcctgtcca atcacagatg    2400
gtcacatgct gctttcctga gttaacctat taactcaccc ttgttttccca ggcctcagtg    2460 gagctaggct tgtcacgtct tcacagtgac tagattccct cacagtcgag tatatctgcc    2520
actccttgac ttttaaaaca tagtctatgt tcaccctcta atatgaagag cccctttcac    2580
tattttcttt gtctgtgctg gagtcacttc agtggcaagt gttctttggt ctctgccgca    2640
ccctccctct gatgcctctg agaagaggat ttccttttcg tgagaatgtc ttcccattct    2700
tcttaccctc ttgaactcac atgttatgcc acttagatga ggaaattgta gttaaataat    2760
tagaaagata tgacttatct caaatcaatc caagatatac tgaagtattg tttatgagta    2820
agatatcagt cttgacgcag aaagaaaaca ggaatccata aggggaggaa agtgttgaaa    2880
agcaaacctg atacagtggg aaaggtggga gacaccataa ggtgctgaag tgataaaaca    2940
ggccagtgtt tctccactgt atgttttcaa taaatgcttc caaggaagga gagtggggca    3000
tgagtagggg agctacagag ataaaccaac ttttcttacc aggaatgcta cagatagcac    3060
tggtgacacc ggtcaccagt acccaagaca atttaatgtg gaacataagt acaggaatac    3120
acatctttca ttacagagcc atgtatttat tttaatgggc aggagatgct aaataagatc    3180
ttttgaatgg aggaatgcat aaatatatga atgaatgcat acatgaaaga ataaataaat    3240
gctgcctagc accaaggagc gaagatagac tcatatcaag ggaaacaagt atgattaaaa    3300
ataagacccc agagtcacgc tcagtctctt tccagccttt tcatcatccg gtacattcag    3360
acaagtttca gggaaggatc ctatttgtcc catgataatg atgggcaagg ggtggggagt    3420
tatctcatac tccgcctgtg gatgagggggt cttctcaggt aaggctctta aatcctaggc    3480
ctgagtaaat ttttttcaaat tttatttttag acagggtccc tctctgttgc ctaggctgga    3540
gtgcagcggc acaatcacag ctcaatgcag cctcaacctc ccaggcccaa gtgatcctcc    3600
cacctcagcc tcttcagtga ctaggactac aggtgcatga ctccatgctt ggctaacttt    3660
aaaaaatgtt tgtttgtttg tttgttttttt acagagatgg ggtctcacca tgttgcccag    3720
gctgatcttg aactcctggg ctcaagtgat tcccctgcct cggcctcctg aaattctggg    3780
attataggct tgagccacca tgcctggctc tgagtaaaga ttaagggaag ccatggtgct    3840
atcgcaatag ggtaccaggc agcttaacaa aggcagaagg gaacctcaga gaaccccgaa    3900
gagccaccgt aaagtgagtg ctgggggagc tgaacttcag tcagtacagg agccgaacag    3960
ccatcaggtg cgcagtgtta gtaattccac cctctgccct gggagcaagg tgtgtggaga    4020
aacctgtagc actttatgac catcagaacc agccttttc aaaagacca tggagtactc    4080 tttgacctgt gtatataaca agaacctttc tcaaatagga aagaaatgaa ttggagaaaa    4140
ccactgttta catggcagag tgtgtctcct tcgcacacat cttgtttgaa gttaatcatg    4200
acattgcaac accaagtgat tccaaataat ctgctaggag tcaccatttc taatgattgc    4260
ctagtctatt catagctaat caagaggatg ttataaagca tgagtcagac acctctggct    4320
ttctggaagg gcaaggactc tatatataca gagggagctt cctagctggg atattggagc    4380
agcaagaggc tgggaagcca tcacttacct tgcactgaga aagaagacaa aggccagt     4438
```

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:Synthetic

```
<400> SEQUENCE: 4
gtggaagctt acacctataa tcccaacact c                              31

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence:Synthetic

<400> SEQUENCE: 5
ctgcctggta ccctattgcg atagcaccat ggc                            33

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence:Synthetic

<400> SEQUENCE: 6
aaataattag aaagatatga cttatctcaa atcaa                          35

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:Synthetic

<400> SEQUENCE: 7
aaataattag aaaggatatg acttatctca aatcaa                         36

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence:Synthetic

<400> SEQUENCE: 8
ttcattgtta atcaagagga tgttataaag catgagtcac accctcagct t         51

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 9
gttatgccac ttagatgagg                                           20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 10
ttcctcccct tatggattcc                                           20
```

INHIBITORY IMMUNOGLOBULIN POLYPEPTIDES TO HUMAN PDGF BETA RECEPTOR

CROSS-REFERENCE TO RELATED APPLICATION

This application is a continuation of application Ser. No. 08/258,283, filed Jun. 10, 1994, issued as U.S. Pat. No. 5,817,310 on Oct. 6, 1998, which is a continuation-in-part of application Ser. No. 08/253,440 filed Jun. 7, 1994, now abandoned, which is a continuation of application Ser. No. 07/801,795, filed Dec. 2, 1991, now abandoned.

FIELD OF THE INVENTION

The present invention relates generally to the production and use of immunoglobulin polypeptides that inhibit PDGF-mediated proliferation of cells displaying the human type beta platelet derived growth factor receptor.

BACKGROUND OF THE INVENTION

Platelet derived growth factor (PDGF) is a potent proliferative agent in cells of mesenchymal origin (Antoniades, H. N. et al. (1979) *Proc. Natl. Acad. Sci. USA* 76:1809–1813; Bowen-Pope, D. F. and Ross, R. (1982) *J. Biol. Chem.* 257:5161–5171; Heldin, C-H. et al. (1983) *J. Biol. Chem.* 258:10054–10059, all of which are incorporated herein by reference). PDGF (M.W. 30 KDa) is a disulfide-linked dimer consisting of 2 homologous chains termed A or B (Johnsson, A. et al. (1982) *Biochem. Biophys. Res. Commun.* 104: 66–74, which is incorporated herein by reference). The chains may combine with chains of the same or the other type, resulting in 3 isoforms AA, BB or AB (Heldin, C-H. et al. (1986) *Nature* 319:511–514, which is incorporated herein by reference). The mitogen PDGF was first identified (Antoniades, H. N. (1979) *Proc. Natl. Acad. Sci. USA* 76:1809–1813; Raines, E. W. and Ross, R. (1982) *J. Biol. Chem.* 257:5154–5160, both of which are incorporated herein by reference) and purified from human platelets (Raines, op. cit.), though subsequent research has shown that several cell types including vascular endothelial cells, vascular smooth muscle cells, macrophages and even fibroblasts synthesize PDGF (Ross, R. et al. (1986) *Cell* 46:155–169, which is incorporated herein by reference).

The cellular proliferation induced by all isoforms of PDGF is mediated by ligand binding to the PDGF receptor (Heldin, C-H. (1983) op. cit., Ek, B. et al. (1982) *Nature* 295:419–420; Glenn, K. et al. (1982) *J. Biol. Chem.* 257: 5172–5176; Frackelton, A. R. et al. (1984) *J. Biol. Chem.* 259:7909–7915; Williams, L. T. et al. (1984) *J. Biol. Chem.* 259:5287–5294, all of which are incorporated herein by reference). The PDGF receptor (M.W. 180 KDa) belongs to the tyrosine kinase family and consists of two receptor subtypes, termed type A (or type alpha) (Matsui, T. et al. (1989) *Science* 243:800–804, and Claesson-Welsh, L. (1989) *Proc. Natl. Acad. Sci. USA* 86:4917–4921, both of which are incorporated herein by reference) and type B (or type beta) (Yarden, Y. et al. (1986) *Nature* 323:226–232, and Escobedo, J. A. et al. (1988) *Science* 240:1532–1534, both of which are incorporated herein by reference).

High affinity binding of PDGF to the receptor is followed by receptor dimerization (Bishayee, S. et al. (1989) *J. Biol. Chem.* 264:11699–11705, and Heldin, C-H. et al. (1989) *J. Biol. Chem.* 264:8905–8912) and autophosphorylation (Frackelton, et al. op. cit.), and results in a complicated series of intracellular signalling events culminating in DNA synthesis. Mouse and human PDGF beta receptor and PDGF alpha receptor genes have been cloned (Matsui et al. op. cit., Claesson-Welsh et al. op. cit., Yarden et al. op. cit., and Escobedo et al. op. cit.). When referring to PDGF receptors herein, type A and type alpha or α-PDGFR are used interchangeably, as are type B and type beta or β-PDGFR.

The two receptor isoforms may be distinguished by their markedly different ligand binding specificities. PDGF beta receptor binds only B-chain (isoforms BB and AB), while PDGF alpha receptor can bind all forms of PDGF (isoforms containing A and/or B chain (Matsui et al. op. cit., Claesson-Welsh et al. op. cit., and Seifert, R. A. et al. (1989) *J. Biol. Chem.* 264:8771–8778). The PDGF receptor shows a high degree of structural homology to the macrophage-colony stimulating factor receptor (Coussens, L. et al. (1986) *Nature* 320:277–280) and the c-kit protooncogene product (Yarden, et al., op. cit.).

The PDGF receptors are characterized by an extracellular domain which may be demarcated into five Ig-like domains (Domains or D 1-5) based on their β-sheet rich structure. These Ig repeats of approximately 100 amino acids each have regularly spaced cysteine residues (except in the fourth repeat). The receptor has a single transmembrane domain and a cytoplasmic tyrosine kinase domain (Williams, L. T. (1989) *Science* 243:1564–1570, which is incorporated herein by reference).

PDGF plays an important role during normal physiological processes such as tissue repair and embryogenesis (Ross, R. et al. op. cit.). However, studies now implicate this potent mitogen in pathological proliferative disorders and in the development of certain carcinomas (Ross, R. et al. op. cit.). Expression of PDGF A chain and PDGF beta receptor has been detected in human atherosclerotic plaques by in situ hybridization (Wilcox, J. N. et al. (1988) *J. Clin. Invest.* 82:1134–1143). Recently, Ferns et al. ((1991) *Science* 253: 1129–1132) have reported that a polyclonal antibody to PDGF significantly reduced the formation of intimal lesions in deendothelialized carotid arteries of athymic nude rats. PDGF has been implicated in the pathology of proliferative diseases in cells of mesenchymal origin (Nister, M. et al. (1984) *Proc. Natl. Acad. Sci. USA* 81:926–930, and Nister, M. et al. (1987) *Cancer Res.* 47:4953–4961, both of which are incorporated herein by reference). Golden et al. have reported that PDGF A chain message was increased in areas of intimal hyperplasia in a baboon model for vascular grafts ((1990) *J. Vasc. Surg.* 11:580–585). PDGF is also chemotactic for smooth muscle (Westermark, B. et al. (1990) *Proc. Natl. Acad. Sci. USA* 87:128–132), and platelet PDGF may be the causative agent for the migration and proliferation of smooth muscle cells in the ballooned rat carotid artery, which results in significant stenosis.

The study of other growth factors and their receptors has been aided by the invention of antibodies against the receptors. For example, antibodies that recognize the epidermal growth factor receptor have proved to be powerful tools in evaluating the mechanism of receptor activation (Spaargaren, M. et al. (1991) *J. Biol. Chem.* 266:1733–1739, which is incorporated herein by reference). Antibodies against receptors for interleukin-2 (IL-2) inhibit IL-2 internalization, and thus inhibit the subsequent induction of proliferation of responsive cells (Duprez, V. et al. (1991) *J. Biol. Chem.* 1497–1501, which is incorporated herein by reference). Similarly, a monoclonal antibody against the epidermal growth factor (EGF) receptor inhibits estrogen-stimulated growth of the human mammary adenocarcinoma cell line MCF-7 (Eppstein, D. A. (1989) *J. Cell. Physiol.* 141:

420–430, which is incorporated herein by reference). Such antibodies may be of great therapeutic value in treating growth factor-mediated diseases.

Several groups have isolated antibodies against PDGF receptors, but these antibodies have limited utility (see, for example, Kawahara, R. S. et al. (1987) *Biochem. Biophys. Res. Commun.* 147:839–845, which is incorporated herein by reference). Additional monoclonal antibodies have been raised against the extracellular PDGF-binding domain of a PDGF receptor from porcine uterus (Ronnestrand, L. and Terracio, L. (1988) *J. Biol. Chem.* 263:10429–10435, which is incorporated herein by reference), but these antibodies did not inhibit binding of $^{125}$I-labelled PDGF to human fibroblasts. Numerous antibodies against a PDGF receptor that did not inhibit PDGF activity have also been reported by Kanakaraj, P. S. et al. (1991) *Biochemistry* 30:1761–1767; Claesson-Welsh, L. et al. (1989) *J. Biol. Chem.* 264:1742–1747; Seifert, R. A. et al. (1989) *J. Biol. Chem.* 264:8771–8778; Kumjian, D. A. et al. (1989) *Proc. Natl. Acad. Sci. USA* 86:8232–8236; Bishayee, S. et al. (1988) *Mol. Cell. Biol.* 8:3696–3702; Hart, C. E. et al. (1987) *J. Biol. Chem.* 262:10780–10785; Escobedo, J. A. et al. (1988) *J. Biol. Chem.* 263:1482–1487; Daniel, T. O. et al. (1987) *J. Biol. Chem.* 262:9778–9784; Keating, M. T. and L. T. Williams (1987) *J. Biol. Chem.* 262:7932–7937; Kazlauskas, A. and J. A. Copper (1990) *EMBO J.* 9:3279–3286; all of which are incorporated herein by reference.

Thus, there exists a need for immunoglobulin and other agents capable of specifically inhibiting activation of the human receptor and/or proliferation of cells displaying the human type beta PDGF receptor. Such agents would be useful in mapping the different functional domains of the receptor, and in dissecting the role of PDGF and its receptors in normal and disease processes. Furthermore, such agents will have therapeutic value in the treatment of PDGF-mediated proliferative diseases, and also diseases involving PDGF-mediated chemotaxis and migration. Such diseases include:

a) restenosis, including coronary restenosis after angioplasty, atherectomy, or other invasive methods of plaque removal, and renal or peripheral artery restenosis after the same procedures;

b) vascular proliferative phenomena and fibrosis associated with other forms of acute injury such as: pulmonary fibrosis associated with adult respiratory distress syndrome, renal fibrosis associated with nephritis, coronary stenosis associated with Kawasake's disease, and vascular narrowings associated with other arteritides such as Takayasha's disease;

c) prevention of narrowings in vein grafts;

d) prevention of narrowings due to accelerated smooth muscle cell migration and proliferation in transplanted organs;

e) other fibrotic processes, such as scleroderma, myofibrosis; and f) inhibition of tumor cell proliferation which is mediated by PDGF.

The present invention fulfills these and other needs.

SUMMARY OF THE INVENTION

The present invention provides immunoglobulin polypeptides that specifically bind to a human type beta platelet derived growth factor receptor (βPDGF-R), wherein binding of the immunoglobulin polypeptide to the second Ig-like domain of a human βPDGF-R has one or more of the following effects: i) inhibition of PDGF BB binding to the receptor; ii) inhibition of PDGF-induced βPDGF-R phosphorylation; iii) inhibition of PDGF-induced dimerization of βPDGF-R; iv) inhibition of PDGF-induced mitogenesis of cells displaying human βPDGF-R; and v) PDGF-induced chemotaxis and migration of cells displaying βPDGF-R. A preferred embodiment of the invention is a monoclonal antibody, such as the monoclonal antibody 2A1E2, which is of the IgG$_1$ isotype.

Isolated nucleic acids having a sequence substantially identical to those coding for all or part of an immunoglobulin polypeptide having the described properties are also included in the invention. A cell line transfected, transformed, or infected with these nucleic acids is another embodiment of the invention, as is a method of producing the immunoglobulin polypeptide or fragments thereof by growing a cell line containing the claimed nucleic acids and harvesting the immunoglobulin polypeptides or fragments.

The immunoglobulin polypeptides of the invention have diagnostic as well as therapeutic uses. For example, a further aspect of the invention involves methods of treating a human having a PDGF-mediated disease involving proliferation of smooth muscle cells, comprising administering to the patient a therapeutically effective dose of an immunoglobulin polypeptide of the present invention.

DESCRIPTION OF THE PREFERRED EMBODIMENTS

Figure 1:
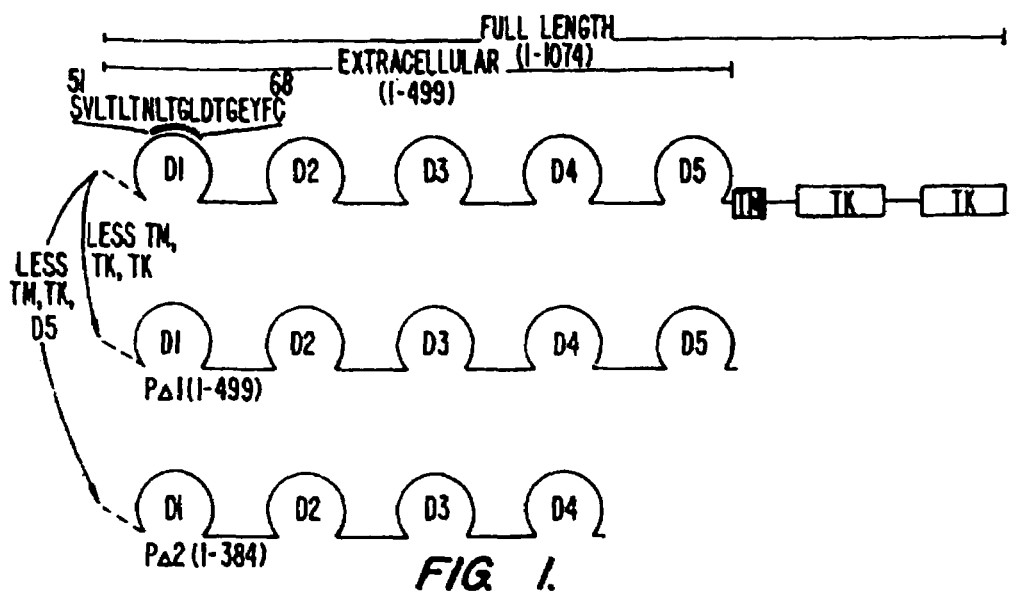
FIG. 1. Recombinant Human Beta Receptor Extracellular Domain Constructs. Deletion mutagenesis of the full length PDGF beta receptor was performed as described in Methods. pΔ1 refers to the 5 domain extracellular PDGF beta receptor (amino acids 1–499) which was made by deleting, from the PDGF type beta receptor cDNA, the codons for amino acid residues 500–1074 using the oligonucleotide GTG TGA GGA ACG GGA AAT TCA TCG AAG GAC ATC CCC CGAC. pΔ2 refers to the 4 domain extracellular PDGF receptor (aa 1–384) which was made by deleting the codons for amino acid residues 385–1074 from the cDNA, using the oligonucleotide GGA AGG TCG ATG TCT AGT TAA TCG AAG GAC ATC CCC CGAC. Putative Ig domains are indicated as follows: D1 (aa 1–91), D2 (aa 92–181), D3 (aa 182–282), D4 (aa 283–384) and D5 (aa 385–499). The peptide determinant of the polyclonal antisera 1-3-5 is indicated above D1.

The present invention provides an immunoglobulin polypeptide that specifically binds to the human type beta PDGF receptor. The antibody is capable of inhibiting PDGF-induced mitogenesis of cells that display the human beta type PDGF receptor on the cell surface. The invention will be useful in diagnostic applications, and also for treating diseases involving PDGF-mediated proliferation, migration and chemotaxis of cells displaying the human type beta PDGF receptor.

Definitions a) Proteins.

The terms "peptide", "polypeptide" or "protein" are used interchangeably herein. The term "substantial identity", when referring to polypeptides, indicates that the polypeptide or protein in question is at least about 30% identical to an entire naturally occurring protein or a portion thereof, usually at least about 70% identical, and preferably at least about 95% identical.

As used herein, the terms "isolated", "substantially pure" and "substantially homogenous" are used interchangeably and describe a protein that has been separated from components which naturally accompany it. Typically, a monomeric protein is substantially pure when at least about 60 to 75% of a sample exhibits a single polypeptide backbone. Minor variants or chemical modifications typically share the same polypeptide sequence. A substantially purified protein will typically comprise over about 85 to 90% of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band on a polyacrylamide gel upon staining. For certain purposes high resolution will be needed and HPLC or a similar means for purification utilized.

A polypeptide is substantially free of naturally-associated components when it is separated from the native contaminants which accompany it in its natural state. Thus, a polypeptide which is chemically synthesized or synthesized in a cellular system different from the cell from which it naturally originates will be substantially free from its naturally-associated components.

Proteins may be purified to substantial homogeneity by standard techniques well known in the art, including selective precipitation with such substances as ammonium sulfate, column chromatography, immunopurification methods, and others. See, for instance, R. Scopes, *Protein Purification: Principles and Practice,* Springer-Verlag: New York (1982), which is incorporated herein by reference.

b) Nucleic Acids.

Nucleic acids, as used herein, may be DNA or RNA. When referring to nucleic acids, the term "substantial identity" indicates that the sequences of two nucleic acids, or designated portions thereof, when optimally aligned and compared, are identical, with appropriate nucleotide insertions or deletions, in at least about 80% of the nucleotides, usually at least about 90% to 95%, and more preferably at least about 98 to 99.5% of the nucleotides.

Alternatively, substantial nucleic acid sequence identity exists when a nucleic acid segment will hybridize under selective hybridization conditions, to a complement of another nucleic acid strand.

"Substantially complementary" similarly means that one nucleic acid hybridizes selectively to, or is identical to, another nucleic acid. Typically, selective hybridization will occur when there is at least about 55% identity over a stretch of at least 14–25 nucleotides, preferably at least about 65% identity, more preferably at least about 75%, and most preferably at least about 90% identity. See, M. Kanehisa *Nucleic Acids Res.* 12:203 (1984), which is incorporated herein by reference.

Stringent hybridization conditions will typically include salt concentrations of less than about 1 M, more usually less than about 500 mM and preferably less than about 200 mM. Temperature conditions will typically be greater than 22° C., more typically greater than about 30° C. and preferably in excess of about 37° C. As other factors may dramatically affect the stringency of hybridization, including base composition and size of the complementary strands, presence of organic solvents and extent of base mismatching, the combination of parameters is more important than the absolute measure of any one alone.

"Isolated" or "substantially pure", when referring to nucleic acids, refer to those that have been purified away from other cellular components or other contaminants, e.g., other cellular nucleic acids or proteins, by standard techniques, including alkaline/SDS treatment, CsCl banding, column chromatography, and others well known in the art. See, F. Ausubel, et al., ed. *Current Protocols in Molecular Biology,* Greene Publishing and Wiley-Interscience, New York (1987), incorporated herein by reference.

A nucleic acid is "operably linked" when it is placed into a functional relationship with another nucleic acid sequence. For instance, a promoter or enhancer is operably linked to a coding sequence if it affects the transcription of the sequence. Generally, operably linked means that the nucleic acid sequences being linked are contiguous and, where necessary to join two protein coding regions, contiguous and in reading frame.

Techniques for nucleic acid manipulation, such as subcloning nucleic acid sequences encoding polypeptides into expression vectors, labelling probes, DNA hybridization, and so on are described generally, for example in Sambrook et al. (1989) *Molecular Cloning: A Laboratory Manual* (2nd ed.), Vols. 1–3, Cold Spring Harbor Laboratory, or Ausubel et al., ed. (1987) op. cit., both of which are incorporated herein by reference.

"Expression vectors", "cloning vectors", or "vectors" are often plasmids or other nucleic acid molecules that are able to replicate in a chosen host cell. Expression vectors may replicate autonomously, or they may replicate by being inserted into the genome of the host cell, by methods well known in the art. Vectors that replicate autonomously will have an origin of replication or autonomous replicating sequence (ARS) that is functional in the chosen host cell(s). Often, it is desirable for a vector to be usable in more than one host cell, e.g., in E. coli for cloning and construction, and in a mammalian cell for expression.

Mammalian cell lines are often used as host cells for the expression of polypeptides derived from eukaryotes. Propagation of mammalian cells in culture is per se well known. See, *Tissue Culture,* Academic Press, Kruse and Patterson, ed. (1973), incorporated herein by reference. Host cell lines may also include such organisms as bacteria (e.g., E. coli or B. subtilis), yeast, filamentous fungi, plant cells, or insect cells, among others.

"Transformation" refers to the introduction of vectors containing the nucleic acids of interest directly into host cells by well known methods. Transformation methods, which vary depending on the type of host cell, include electroporation; transfection employing calcium chloride, rubidium chloride calcium phosphate, DEAE-dextran, or other substances; microprojectile bombardment; lipofection; infection (where the vector is an infectious agent); and other methods. See generally, Sambrook et al., (1989) op. cit. and Ausubel et al. (ed.), (1987) op. cit. Reference to cells into which the nucleic acids described above have been introduced is meant to also include the progeny of such cells.

c) Antibodies.

As used herein, "immunoglobulin polypeptide" refers to molecules which have specific immunoreactive activity. Antibodies are typically tetramers of immunoglobulin polypeptides. As used herein, the term "antibody" refers to a protein consisting of one or more polypeptides substantially encoded by immunoglobulin genes. Immunoglobulin genes include those coding for the light chains, which may be of the kappa or lambda types, and those coding for the heavy chains, Heavy chain types are alpha, gamma, delta, epsilon and mu. The carboxy terminal portions of immunoglobulin heavy and light chains are constant regions, while the amino terminal portions are encoded by the myriad immunoglobulin variable region genes. The variable regions of an immunoglobulin are the portions that provide antigen recognition specificity. In particular, the specificity resides in the complementarity determining regions (CDRs), also known as hypervariable regions, of the immunoglobulins. The immunoglobulins may exist in a variety of forms including, for example, Fv, Fab, F(ab'), F(ab')$_2$, and other fragments, as well as single chains (e.g., Huston, et al., Proc. Nat. Acad. Sci. U.S.A., 85:5879–5883 (1988) and Bird, et al., Science 242:423–426 (1988), which are incorporated herein by reference). (See, generally, Hood, et al., "Immunology", Benjamin, N.Y., 2nd ed. (1984), and Hunkapiller and Hood, *Nature,* 323:15–16 (1986), which are incorporated herein by reference). Single-chain antibodies, in which genes for a heavy chain and a light chain are combined into a single coding sequence, may also be used. Immunoglobulin polypeptide also encompasses a chain containing less constant region domains than in the native polypeptide. Such truncated polypeptides can be produced by standard methods such as introducing a stop codon into the gene sequence 5' of the domain sequences to be deleted. The truncated polypeptides can then be assembled into truncated antibodies. Antibodies as used herein also include bispecific antibodies which can be produced such as by the methods described in the following references: Glennie et al. *J. Immunol.* 139:2367–2375 (1987); Segal et al. *Biologic Therapy of Cancer Therapy of Cancer Updates* 2(4):1–12 (1992); and Shalaby et al. *J. Exp. Med.* 175:217–225 (1992).

"Monoclonal antibodies" may be obtained by various techniques familiar to those skilled in the art. Briefly, spleen cells from an animal immunized with a-desired antigen are immortalized, commonly by fusion with a myeloma cell (see, Kohler and Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

Monospecific and bispecific immunoglobulins may also be produced by recombinant techniques in prokaryotic or eukaryotic host cells.

"Chimeric" antibodies are encoded by immunoglobulin genes that have been genetically engineered so that the light and heavy chain genes are composed of immunoglobulin gene segments belonging to different species. For example, the variable (V) segments of the genes from a mouse monoclonal antibody may be joined to human constant (C) segments. Such a chimeric antibody is likely to be less antigenic to a human than antibodies with mouse constant regions as well as mouse variable regions.

As used herein, the term chimeric antibody also refers to an antibody that includes an immunoglobulin that has a human-like framework and in which any constant region present has at least about 85–90%, and preferably about 95% polypeptide sequence identity to a human immunoglobulin constant region, a so-called "humanized" immunoglobulin (see, for example, PCT Publication WO 90/07861, which is incorporated herein by reference). Hence, all parts of such a "humanized" immunoglobulin, except possibly the complementarity determining regions (CDR's), are substantially identical to corresponding parts of one or more native human immunoglobulin sequences. Where necessary, framework residues may also be replaced with those within or across species especially if certain framework residues are found to affect the structure of the CDRs. A chimeric antibody may also contain truncated variable or constant regions.

The term "framework region", as used herein, refers to those portions of immunoglobulin light and heavy chain variable regions that are relatively conserved (i.e., other than the CDR's) among different immunoglobulins in a single species, as defined by Kabat, et al., (1987): *Sequences of Proteins of Immunologic Interest,* 4th Ed., US Dept. Health and Human Services, which is incorporated herein by reference). As used herein, a "human-like framework region" is a framework region that in each existing chain comprises at least about 70 or more amino acid residues, typically 75 to 85 or more residues, identical to those in a human immunoglobulin.

Human constant region DNA sequences can be isolated in accordance with well known procedures from a variety of human cells, but preferably from immortalized B-cells. The variable regions or CDRs for producing the chimeric immunoglobulins of the present invention may be similarly derived from monoclonal antibodies capable of binding to the human type beta PDGF receptor, and will be produced in any convenient mammalian system, including, mice, rats, rabbits, human cell lines, or other vertebrates capable of producing antibodies by well known methods. Variable regions or CDRs may be produced synthetically, by standard recombinant methods including polymerase chain reaction (PCR) or through phage-display libraries. For phage display methods, see for example, McCafferty et al. *Nature:*348: 552–554 (1990); Clackson et al. *Nature* 352:624–628; and Marks et al. *Biotechnoloy* 11:1145–1149 (1993). Suitable prokaryotic systems such as bacteria, yeast and phage may be employed.

Suitable source cells for the DNA sequences and host cells for immunoglobulin expression and secretion can be obtained from a number of sources, such as the American Type Culture Collection ("Catalogue of Cell Lines and Hybridomas," Fifth edition (1985) Rockville, Md., U.S.A., which is incorporated herein by reference).

In addition to the chimeric and "humanized" immunoglobulins specifically described herein, other substantially identical modified immunoglobulins can be readily designed and manufactured utilizing various recombinant DNA techniques well known to those skilled in the art. In general, modifications of the genes may be readily accomplished by a variety of well-known techniques, such as PCR and site-directed mutagenesis (see, Gillman and Smith, *Gene* 8:81–97 (1979) and S. Roberts et al., *Nature* 328:731–734 (1987), both of which are incorporated herein by reference).

Alternatively, polypeptide fragments comprising only a portion of the primary immunoglobulin structure may be produced. For example, it may be desirable to produce immunoglobulin polypeptide fragments that possess one or more immunoglobulin activities in addition to, or other than, antigen recognition (e.g., complement fixation).

Immunoglobulin genes, in whole or in part, may also be combined with functional regions from other genes (e.g., enzymes), or with other molecules such as toxins, labels and targeting moieties to produce fusion proteins (e.g., "immunotoxins") having novel properties. In these cases of gene fusion, the two components are present within the same polypeptide chain. Alternatively, the immunoglobulin or fragment thereof may be chemically bonded to the toxin or label by any of a variety of well-known chemical procedures. For example, when the label or cytotoxic agent is a protein and the second component is an intact immunoglobulin, the linkage may be by way of heterobifunctional cross-linkers, e.g., SPDP, carbodiimide, glutaraldehyde, or the like.

Suitable labels include, for example, radionuclides, enzymes, substrates, cofactors, inhibitors, fluorescers, chemiluminescers, magnetic particles. See, for examples of patents teaching the use of such labels, U.S. Pat. Nos. 3,817,837; 3,850,752; 3,939,350; 3,996,345; 4,277,437; 275,149; and 4,366,241, all of which are incorporated by reference.

Immunotoxins, including single chain molecules, may also be produced by recombinant means. Production of various immunotoxins is well-known with the art, and methods can be found, for example in "Monoclonal Antibody-Toxin conjugates: Aiming the Magic Bullet," Thorpe et al, *Monoclonal Antibodies in Clinical Medicine,* Academic Press, pp. 168–190 (1982); E. Vitetta, *Science* (1987) 238:1098–1104; and G. Winter and C. Milstein, *Nature* (1991) 349:293–299; all incorporated herein by reference.

A variety of cytotoxic agents are suitable for use in immunotoxins. Cytotoxic agents can include radionuclides, such as Iodine-131, Yttrium-90, Rhenium-188, and Bismuth-212; a number of chemotherapeutic drugs, such as vindesine, methotrexate, adriamycin, and cisplatinum; and cytotoxic proteins such as ribosomal inhibiting proteins like pokeweed antiviral protein, Pseudomonas exotoxin A, ricin, diphtheria toxin, ricin A chain, etc., or an agent active at the cell surface, such as the phospholipase enzymes (e.g., phospholipase C). (See, generally, "Chimeric Toxins," Olsnes and Pihl, *Pharmac. Ther.,* 15:355–381 (1981), and "Monoclonal Antibodies for Cancer Detection and Therapy," eds. Baldwin and Byers, pp. 159–179, 224–266, Academic Press (1985), both of which are incorporated herein by reference).

Description of the Invention

The immunoglobulin polypeptides of the present invention will find use in therapeutics as well as in diagnostics and other applications. Various techniques useful in these arts are discussed, for example, in Harlow and Lane, *Antibodies: A Laboratory Manual,* Cold Spring Harbor, N.Y. (1988) (incorporated herein by reference for all purposes), including: immunization of animals to produce immunoglobulins; production of monoclonal antibodies; labeling immunoglobulins for use as probes; immunoaffinity purification; and immunoassays.

An example of an immunoglobulin polypeptide of the present invention is the monoclonal antibody 2A1E2, described below, which binds specifically to the type beta human PDGF receptor. Monoclonal antibody 2A1E2, which is of the IgG$_1$ isotype, was deposited with the American Type Culture Collection, 12301 Park Lawn Drive, Rockville, Md. 20231 (ATCC no. HB10938), prior to the filing date of this application.

The anti-PDGF receptor immunoglobulin polypeptides of the present invention may be prepared by immunizing an animal with a purified or partially purified extracellular domain of human beta-type PDGF receptor. The animals immunized can be any one of a variety of species which are capable of immunologically recognizing epitopes characteristic of the human type beta PDGF receptor extracellular domain, such as murine, lagomorph, equine, etc.

Monoclonal antibodies of the invention may be prepared by immortalizing nucleic acid sequences which encode immunoglobulin polypeptides or portions thereof that bind specifically to antigenic determinants characteristic of the extracellular domain of the human type beta PDGF receptor. The immortalization process can be carried out by hybridoma fusion techniques, by viral transformation of antibody-producing lymphocytes, recombinant DNA techniques, or by techniques that combine cell fusion, viral transformation and/or recombinant DNA methodologies.

According to one aspect of the invention, cells producing human anti-PDGF receptor monoclonal antibodies are immortalized using, e.g., Epstein-Barr virus (EBV) transformation techniques. For example, B lymphocytes derived from peripheral blood, bone marrow, lymph nodes, tonsils, etc. of patients, preferably those immunized with the PDGF receptor or portions thereof, are immortalized using EBV according to methods such as those described in U.S. Pat. No. 4,464,465, and Chan et al., *J. Immunol.* 136:106 (1986), which are incorporated herein by reference.

Human anti-PDGF receptor monoclonal antibodies can also be prepared by a variety of other ways, e.g., using a combination of EBV or other viral transformation and hybridoma fusion techniques. For instance, the hybridomas can be created by fusing stimulated B cells, obtained from a individual immunized with the PDGF receptor or a portion thereof, with a mouse/human heterohybrid fusion partner, a variety of which have been described. See, e.g., U.S. Pat. No. 4,624,921 and James and Bell, *J. Immunol. Meths.* 100:5–40 (1987), which are incorporated herein by reference. A mouse/human fusion partner can be constructed by fusing human lymphocytes stimulated or transformed by EBV with readily available mouse myeloma lines such as NS-1 or P3NS-1, in the presence of, e.g., polyethylene glycol. The hybrid should be suitably drug-marked, which can be accomplished by cultivating the hybrid in increasing concentrations of the desired drug, such as 6-thioguanine, ouabain, or neomycin.

The hybridomas or lymphoblastoid cells which secrete antibody of interest can be identified by screening culture supernatants for antibody that binds to the type beta PDGF receptor. More preferably, a screening assay may be employed to detect those antibodies which inhibit, for example, PDGF-mediated mitogenesis. Cells which possess the desired activity are cloned and subcloned in accordance with conventional techniques and monitored until stable, immortalized lines producing the anti-PDGF receptor monoclonal antibody of interest are identified. By monoclonal antibody is meant an antibody produced by a clonal, immortalized cell line separate from cells producing antibodies with a different antigen binding specificity. Thus, such monoclonal antibodies are produced isolated from other monoclonal antibodies and, accordingly, in substantially pure form (relative to other antibodies) and at a concentration generally greater than normally occurring in sera from the animal species which serves as a B cell source.

Alternatively, one can isolate DNA sequences which encode a human anti-PDGF receptor immunoglobulin polypeptide or portions thereof that specifically bind to the extracellular domain of the PDGF receptor by screening a DNA library from human B cells according to a general protocol as outlined by Huse et al., *Science* 246:1275–1281 (1989), incorporated herein by reference, and then cloning and amplifying the sequences which encode the anti-PDGF receptor antibodies (or binding fragment) of the desired specificity.

The immunoglobulins may then be produced by introducing an expression vector containing the appropriate immunoglobulin gene, or portion thereof, into an appropriate host cell. The host cell line is then maintained under conditions suitable for high level expression of the immunoglobulin nucleotide sequences, and, as desired, the collection and purification of the light chains, heavy chains, light/heavy chain diners or intact antibodies, binding fragments or other immunoglobulin forms may follow.

Suitable host cells include microorganisms, but mammalian or insect tissue cell culture may be preferable for producing the monoclonal antibody of the present invention (see, E. Winnacker, "From Genes to Clones," VCH Publishers, N.Y., N.Y. (1987), which is incorporated herein by reference). A number of suitable mammalian host cell lines capable of secreting intact immunoglobulins have been developed in the art, and include the Chinese hamster ovary (CHO) cell line, but preferably hybridomas or transformed B-cells will be used. Bacterial phage or yeast systems may also be employed.

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, generally, R. Scopes, *Protein Purification,* Springer-Verlag, N.Y. (1982), incorporated herein by reference). Substantially pure immunoglobulins of at least about 90 to 95% homogeneity are preferred, and those of 98 to 99% or greater homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. (See, generally, *Immunological Methods,* Vols. I and II, Lefkovits and Pernis, eds., Academic Press, New York, N.Y. (1979 and 1981), which are incorporated herein by reference).

The immunoglobulin polypeptides produced according to the present invention may be of the IgG, IgM, IgA or IgD isotype, and may further be any of the appropriate subclasses thereof, such as, e.g., $IgG_1$, $IgG_2$, $IgG_3$, or $IgG_4$. Using recombinant DNA techniques, "class-switching" of the isolated immunoglobulin polypeptides may be readily accomplished. In this method genes encoding the constant regions which determine the isotype of the immunoglobulin molecule of interest are replaced by genes encoding a desired isotype or subclass, as generally described in European patent publication EP 314,161, incorporated herein by reference. Class-switched immunoglobulins may also be isolated by selecting cells which have undergone spontaneous switching using selection methods known in the art.

The administration to humans of immunoglobulin polypeptides which are substantially non-human may elicit anti-antibody responses. Thus, it may be desirable to prepare anti-PDGF receptor immunoglobulin polypeptides of the present invention which are substantially human. By "substantially human" is meant an antibody or binding fragment thereof comprised of amino acid sequences which are at least about 50% human in origin, at least about 70 to 80% more preferred, and about 95–99% or more human most preferred, particularly for repeated administrations over a prolonged period as may be necessary to treat established PDGF-mediated cell proliferation disorders. As used herein, human antibody is meant to include antibodies of entirely human origin as well as those which are substantially human, unless the context indicates otherwise.

As the generation of human anti-PDGF receptor monoclonal antibodies may be difficult with conventional immortalization techniques, it may be desirable to first make non-human antibodies and then transfer via recombinant DNA techniques the antigen binding regions of the non-human antibodies, e.g., the Fab, complementarity determining regions (CDRs) or hypervariable regions, to human constant regions (Fc) or framework regions as appropriate to produce substantially human molecules. Such methods are generally known in the art and are described in, for example, U.S. Pat. No. 4,816,397, PCT publication WO 90/07861, and EP publications 173494 and 239400, wherein each is incorporated herein by reference. However, completely human antibodies can now be produced in transgenic animals. The desired human immunoglobulin genes or gene segments can be isolated, for example by PCR from human B cells, the DNA cloned into appropriate vectors for expression in eukaryotic cells and the cloned DNA introduced into animals to produce transgenics. Animals suitable for the production of transgenics expressing human immunoglobulins include mice, rats, rabbits and pigs with rodents being preferred. Mice and other animals for the preparation of transgenics that express human immunoglobulins should preferably have one or more of their endogenous immunoglobulin loci inactivated or "knocked-out" to facilitate identification and isolation of the human antibodies (See e.g., Lonberg, et al. *Nature* 368:856–859 (1994)).

The resulting chimeric antibodies or chimeric immunoglobulin polypeptides that specifically bind to the human type beta PDGF receptor and thus inhibit binding of PDGF to the receptor are also within the scope of the present invention. A typical therapeutic chimeric antibody would be a hybrid protein consisting of the variable (V) or antigen-binding domain from a mouse immunoglobulin specific for a human PDGF type beta receptor antigenic determinant, and the constant (C) or effector domain from a human immunoglobulin, although domains from other mammalian species may be used for both variable and constant domains. As used herein, the term "chimeric antibody" also refers to antibodies coded for by immunoglobulin genes in which only the complementarity determining regions (CDR's) are transferred from the immunoglobulin that specifically recognizes the antigenic determinants, the remainder of the immunoglobulin gene being derived from a human (or other mammalian, as desired) immunoglobulin gene. This type of chimeric antibody is referred to as a "humanized" (in the case of a human immunoglobulin gene being used) antibody.

The hypervariable regions of the variable domains of the anti-PDGF receptor immunoglobulin polypeptides comprise a related aspect of the invention. The hypervariable regions, or CDRs, in conjunction with the framework regions (those portions of immunoglobulin light and heavy chain variable regions that are relatively conserved among different immunoglobulins in a single species), enable the anti-PDGF receptor immunoglobulin polypeptides to recognize and thus bind to the human type beta PDGF receptor. The hypervariable regions can be cloned and sequenced. Once identified, these regions that confer specific recognition of the PDGF receptor can then be cloned into a vector for expression in a host as part of another immunoglobulin molecule or as a fusion protein, e.g., a carrier molecule which functions to enhance immunogenicity of the cloned idiotope.

The anti-PDGF receptor immunoglobulin polypeptides of the invention will generally be used intact, or as immunogenic fragments, such as $F_v$, Fab, F(ab'), or F(ab')$_2$ fragments. The fragments may be obtained from antibodies by conventional techniques, such as by proteolytic digestion of the antibody using, e.g., pepsin or papain, or by recombinant DNA techniques in which a gene or portion thereof encoding the desired fragment is cloned or synthesized, and expressed in a variety of hosts.

Those skilled in the art will realize that "anti-idiotypic" antibodies can be produced by using a specific immunoglobulin as an immunogen in accordance with standard techniques. For example, infection or immunization with a PDGF receptor polypeptide, or fragment thereof, induces a neutralizing immunoglobulin, which has on its Fab variable region combining site an image of the PDGF receptor polypeptide that is unique to that particular immunoglobulin, i.e., an idiotype. Immunization with such an anti-PDGF-R immunoglobulin induces an anti-idiotype antibody, which has a conformation at its combining site that mimics the structure of the original PDGF-R antigen. These anti-idiotype antibodies may therefore be used instead of the PDGF-R antigen to treat PDGF-mediated diseases (see, for example, Nisonoff (1991) *J. Immunol.* 147:2429–2438, which is incorporated herein by reference).

The anti-PDGF receptor immunoglobulin polypeptides of the invention find utility in therapeutic and diagnostic methods and compositions. For therapeutic uses, anti-PDGF receptor immunoglobulin polypeptides are used as a soluble ligand for human type beta PDGF receptor, masking the receptor or otherwise inhibiting PDGF molecules from binding to the receptor, and thereby inhibiting the undesired cell migration and proliferation.

For pharmaceutical compositions, the anti-PDGF receptor immunoglobulin polypeptides of the invention as described herein are administered to an individual having a PDGF-mediated cellular proliferation disorder. In therapeutic applications, compositions are administered to a patient in an amount sufficient to effectively block cell receptors, and thereby cure or at least partially arrest the cellular proliferation and its symptoms and/or complications. An amount adequate to accomplish this is defined as "therapeutically effective dose."

Amounts effective for this use will depend on, e.g., the nature of the anti-PDGF receptor immunoglobulin polypeptide composition, the manner of administration, the stage and severity of the disease being treated, the weight and general state of health of the patient, and the judgment of the prescribing physician, but will generally range from about 0.01 mg/kg to about 100.0 mg/kg of antibody per day, with dosages of from about 0.1 mg/kg to about 10.0 mg/kg of antibody per day being more commonly used. It must be kept in mind that the anti-PDGF receptor immunoglobulin polypeptide and peptide compositions derived therefrom may be employed in serious disease states, that is, life-threatening or potentially life threatening situations. In such cases, it is possible and may be felt desirable by the treating physician to administer substantial excesses of these compositions. Thus, human anti-PDGF receptor monoclonal antibodies or substantially human anti-PDGF receptor monoclonal antibodies of the invention are most preferred under these circumstances.

Single or multiple administrations of the compositions can be carried out with dose levels and pattern being selected by the treating physician. In any event, the pharmaceutical formulations should provide a quantity of anti-PDGF receptor immunoglobulin polypeptide of the invention sufficient to effectively treat the patient. Administration should begin at the first indication of undesirable cellular proliferation or shortly after diagnosis, and continue until symptoms are substantially abated and for a period thereafter. In well established cases of disease, loading doses followed by maintenance doses will be required.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the anti-PDGF receptor immunoglobulin polypeptide dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of anti-PDGF receptor immunoglobulin polypeptides of the invention in the pharmaceutical formulations can vary widely, i.e., from less than about 1%, usually at or at least about 10–15% to as much as 50% or more by weight, and will be selected primarily by fluid volumes, viscosities, etc., in accordance with the particular mode of administration selected.

Thus, a typical pharmaceutical composition for intravenous infusion could be made up to contain 250 ml of sterile Ringer's solution, and 100 mg of anti-PDGF receptor immunoglobulin polypeptide. Actual methods for preparing parenterally administrable compounds will be known or apparent to those skilled in the art and are described in more detail in for example, *Remington's Pharmaceutical Science,* 17th ed., Mack Publishing Company, Easton, Pa. (1985), which is incorporated herein by reference.

The anti-PDGF receptor immunoglobulin polypeptides and fragments thereof can also be administered via liposomes. The anti-PDGF receptor immunoglobulin polypeptides can serve to target the liposomes to particular tissues or cells displaying the human type beta PDGF receptor. Liposomes include emulsions, foams, micelles, insoluble monolayers, liquid crystals, phospholipid dispersions, lamellar layers and the like. In these preparations the immunoglobulin polypeptide or fragment to be delivered is incorporated as part of the liposome, alone or in conjunction with a molecule which is, for example, toxic to the target cells. A liposome suspension containing an immunoglobulin polypeptide can be administered intravenously, locally, topically, etc. in a dose which varies according to, inter alia, the manner of administration, the peptide being delivered, and the stage of disease being treated.

For solid compositions of the anti-PDGF receptor immunoglobulin polypeptides of the invention, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more anti-PDGF receptor immunoglobulin polypeptides, and more preferably at a concentration of 25%–75%.

For diagnostic purposes, the anti-PDGF receptor immunoglobulin polypeptides may either be labeled or unlabeled. A label is a substance that provides a detectable signal by any of a variety of techniques well known and reported in the art. The immunoglobulin polypeptides of the invention themselves may be directly labeled. Alternatively, unlabeled antibodies included in the invention may be used in combination with other antibodies (second antibodies) that are labelled and that recognize the anti-PDGF receptor immunoglobulin polypeptides of the present invention. For example, labelled antibodies specific for the constant regions of the anti-PDGF receptor immunoglobulin polypeptides may be used to detect the immunoglobulin polypeptide bound to a sample.

A wide variety of labels may be employed, such as radionuclides, fluors, enzymes, enzyme substrates, enzyme cofactors, enzyme inhibitors, ligands (particularly haptens), etc. Numerous types of immunoassays are available and are well known to those skilled in the art.

The anti-PDGF receptor immunoglobulin polypeptides, and fragments thereof, of the present invention may be used in various immunoassays for detecting PDGF receptor in physiological specimens. Such immunoassay methods may include liquid phase immunoassays and Western blot analysis, competitive and noncompetitive protein binding assays, enzyme-linked immunosorbant assays (ELISA), an others commonly used and widely described in scientific and patent literature, and many employed commercially.

Such immunoglobulins and peptides may likewise be employed in immunohistochemical staining techniques by methods well known in the art.

The following example is offered by way of illustration and not limitation.

EXAMPLE 1

Materials

PDGF BB was purchased from Amgen. Anti-phosphotyrosine monoclonal antibody (MAb) PY20 was purchased from ICI. DMEM, RPMI 1640, F12, calf serum, penicillin-streptomycin solution, G418-Neomycin, 200 mM glutamine, IM HEPES, sodium pyruvate (11 mg/ml), and phosphate buffered saline (PBS) were from GIBCO. Fetal calf serum (FCS) and the monoclonal antibody subtyping kit was from Hyclone. Tris, sodium phosphate, sodium borate, acetic acid, sodium pyrophosphate, sodium fluoride, dithiothreitol (DTT), ethylenediamine tetraacetic acid (EDTA), EGTA, sodium dodecyl sulphate (SDS), sodium orthovanadate, sodium chloride (NaCl), citric acid, phenyl methyl sulphonyl fluoride (PMSF), bovine serum albumin (BSA), Triton X100, Tween 20, 2,2' Azino-bis(3-ethylbenzthiazoline)-6-sulfonic acid (ABTS), and hydrogen peroxide were from Sigma. Goat anti-mouse peroxidase and hypoxanthine-thiamine (HT) were from Boehringer Mannheim. Gelatin, unstained protein molecular weight markers and nitrocellulose were from BioRad. Prestained high molecular weight protein markers were from BRL. Protein A sepharose CL4B, Protein G sepharose CL4B, Immunopure™ binding buffer, F(ab')$_2$ and Fab preparation kits.were from Pierce. Pre-packed PD10 columns were from Pharmacia. $^{125}$I-Protein A and $^{14}$C-molecular weight markers were from Amersham. $^{125}$I-diiodo-Bolton-Hunter reagent was from New England Nuclear. Methanol was from Burdick-Jackson. Tissue culture supplies were from Costar. AG01523B cells were obtained from ATCC. HR5 cells were kindly provided by J. A. Escobedo (UCSF). Primary baboon brachial artery smooth muscle cells were generously provided by J. Anderson and S. Hanson (Emory Univ.).

Methods

Cell culture. NIH 3T3 cells were routinely maintained in DMEM containing 10% fetal calf serum, 1×penicillin-streptomycin, 2 mM glutamine, and sodium pyruvate (0.11 mg/ml). CHO cells expressing the extracellular domain (pΔ1-5) or the full-length PDGF beta receptor (HR5) were cultured in RPMI containing 10% FCS, 1× penicillin-streptomycin, 2 mM glutamine, sodium pyruvate (0.11 mg/ml) and G418 (200 µg/ml). Human foreskin fibroblast cells (AG01523B) were cultured in DMEM containing 10% FCS, 1× penicillin-streptomycin, 2 mM glutamine, and sodium pyruvate (0.11 mg/ml). Monoclonal hybridoma cells were maintained in 50:50 DME:RPMI containing 20% FCS, 1× penicillin-streptomycin, 2 mM glutamine, sodium pyruvate (0.1 mg/ml), 1× HT, and 10% macrophage-conditioned medium.

Construction of Truncated Human PDGF beta receptor-expressing cell lines. Truncation of the human PDGF beta receptor cDNA was performed by oligonucleotide-directed deletion mutagenesis. Oligonucleotide-directed in vitro mutagenesis was performed according to a modified method of Kunkel et al. (1987) *Meth. Enzymol.* 154:367–382, which is incorporated herein by reference). Initially a 3.9 kb EcoRI-HindIII cDNA fragment of the entire coding region of the human PDGF beta receptor (residues −32 to 499) was subcloned into the EcoRI and HindIII sites of m13mp18 generating vector mp18PR (Maniatis, T. et al. (1982) *Molecular Cloning: A Laboratory Manual,* Cold Spring Harbor Laboratory, Cold Spring Harbor, N.Y., which is incorporated herein by reference).

Oligonucleotides were designed to delete the portions of the human PDGF beta receptor cDNA that code for amino acids 499–1074 (PRΔ1; GTG TGA GGA ACG GGA AAT TCA TCG AAG GAC ATC CCC CGAC) (SEQ ID NO:1), or amino acids 384–1074 (PRΔ2; GGA AGG TCG ATG TCT AGT TAA TCG AAG GAC ATC CCC CGAC) (SEQ ID NO:2) (FIG. 1.). A stop codon was introduced after residue 499 (PRΔ1) or residue 384 (PRΔ2). Verification of subcloning was performed by restriction enzyme digestion analysis and dideoxy chain termination sequencing (Sanger, F. et al. (1977) *Proc. Natl. Acad. Sci. USA,* 74:5463–5467, which is incorporated herein by reference).

The modified PDGF beta receptor polypeptides were subcloned into the EcoRI and HindIII sites of the expression vector PBJ1 (Lin, A. et al. (1990) *Science* 249:677–679, which is incorporated herein by reference) and cotransfected with vector pSV2Neo (Southern, P. J. and Berg, P. (1982) *J. Mol. Appl. Gen.* 1:327–341, which is incorporated herein by reference) at a ratio of 1:10 into CHO-K1 cells by the method of lipofectin reagent uptake (Felgner, P. L. et al. (1987) *Proc. Natl. Acad. Sci. USA* 84:7413–7417, which is incorporated herein by reference). Transfected cells were selected for G418-neomycin resistance, and individual clones were isolated and screened at equal cell density for high level expression of extracellular PDGF beta receptor in serum-free medium. Expression of the modified extracellular PDGF beta receptor proteins was determined by Western blot analysis using a rabbit polyclonal serum (Ab 1-3-5, see FIG. 1) raised against a synthetic peptide based on human PDGF receptor residues 51-68 (SVLTLTNLTGLDT-GEYFC) (SEQ ID NO:3). Recombinant clones pΔ1-5 (expressing full-length extracellular PDGF receptor) and pΔ2-7 (expressing domains 1-4 of the extracellular PDGF receptor) were used for subsequent protein production.

Preparation of MAbs against human PDGF beta receptor. Antibodies were developed as described by Harlow and Lane (1988, In Antibodies: A Laboratory Manual, Cold Spring Harbor Laboratory, Cold Spring Harbor, N.Y., which is incorporated herein by reference). Mice were immunized with partially purified extracellular domain of PDGF beta receptor (pΔ1-5) using 50–100 μg/immunization). The titre of antibody in the immunized mice was determined using an enzyme-linked immunosorbant assay (ELISA), as follows. 96-well Immunolon II microtiter plates were coated overnight at 4° C. with partially purified (10–15%) extracellular domain of PDGF beta receptor (200–300 ng/well). The remaining manipulations were conducted at room temperature. The wells were blocked with 0.05 M Tris, pH 7 containing 100 mM NaCl and 0.5% gelatin for 1 hour. Plates were incubated for 2 hours with various dilutions of mouse sera, washed 5× with wash buffer (0.05 M Tris, pH 7, 100 mM NaCl and 0.3% gelatin) and incubated with goat anti-mouse peroxidase (1:1000 in wash buffer) for 1 hour. Plates were washed as previously described and developed with 2,2'-Azino-bis(3-ethylbenzthiazoline)6-sulfonic acid (ABTS, 1 mg/ml) in 0.1 M citric acid, 0.1 M dibasic sodium phosphate, pH 4, containing hydrogen peroxide (0.003% final concentration). The absorbance at 650 nm was determined, and the values were compared to the values obtained with protein purified to a similar extent from conditioned media from CHO cells transfected with the pBJ vector alone.

Mice showing high reactivity were sacrificed and the spleens were isolated. Splenocytes were removed and fused with myeloma cells P3x as described (Harlow and Lane, op. cit.). Hybridomas were screened using the same ELISA, and positive hybridomas were cloned and rescreened. Positive monoclonal cells were cultured and ascites was prepared in Balb/c mice as described (Harlow and Lane, op. cit.). Tissue culture media was used to sub-type the MAbs, using the subtyping kit from Hyclone as instructed by the manufacturer.

Purification of Antibodies. Antibodies were purified on Protein A sepharose CL4B as follows. Ascites fluid was diluted 1:5 in Immunopure™ binding buffer (Pierce) and chromatographed over a Protein A sepharose CL4B column equilibrated in the same buffer. The flow through was collected and the column was washed with Immunopure binding buffer (10 column volumes). The bound IgGs were eluted with 0.1 M glycine, pH 2.8, and collected in tubes containing 2 M Tris, pH 11 (40 μl/ml) as neutralizing agent. The peak protein fractions were detected by measuring the absorbance at 280 nm, pooled and dialyzed in PBS (2 changes of 4 L each).

Preparation of MAb 2A1E2 F(ab')$_2$ and Fab Proteolytic Fragments. F(ab')$_2$ fragments of MAb 2A1E2 were prepared from intact MAb using the Immunopure F(ab')$_2$ preparation kit (Pierce) according to the manufacturer's instructions. Monoclonal antibody 2A1E2 was incubated with immobilized pepsin for 4 hours at 37° C. at pH 4.2, and the uncleaved IgG and Fc fragments were separated from the F(ab')$_2$ fragments using Protein A sepharose CL4B. Fab fragments were similarly prepared using the Pierce Immunopure Fab preparation kit. The IgG was incubated with immobilized papain for 5 hours at 37° C. at pH 7, and undigested IgG and Fc fragments were removed using Protein A. The samples were analyzed by SDS-PAGE after enzymatic digestion, and the PDGF beta receptor ELISA was used to determine loss, if any, of antigen recognition.

Immunoprecipitation Assay. Immunoprecipitations were done by a modification of the procedure of Kessler, S. W. (1981, *Meth. Enzymol.* 73:442–471, which is incorporated herein by reference). When purified pΔ1-5 or pΔ2-7 were used, the protein was incubated with MAb for either 2 hours at room temp or 12 hours at 4° C. in immunoprecipitation (IP) buffer (40 mM Tris, pH 8, 100 mM NaCl, 10 mM EDTA, 1 mM EGTA and 1% Triton X100). If full-length receptor was immunoprecipitated, then cells expressing the PDGF beta receptor were solubilized in IP buffer containing 1 μM sodium orthovanadate and 1 mM PMSF, and incubated with the MAb for 8–12 hours at 4° C. Then the samples were incubated with a 50% slurry of a 1:1 mixture of Protein A-Sepharose CL4B and Protein G-sepharose CL4B (50–100 μl/sample). After 1–2 hours at 4° C., the resin was washed by 3 cycles of centrifugation and resuspension in IP buffer, and finally the resin was boiled in Laemnli sample solubilizing buffer (50–100 μl/sample) (1970, *Nature* 227:680–685, which is incorporated herein by reference). The samples were subjected to SDS-PAGE on a 7% or 10% Laemmli gel, and then transferred to nitrocellulose. The western blot was blocked in blocking buffer (0.05 M Tris, pH 8 containing 0.5% NaCl and 4% BSA), and incubated with the primary antibody for 12 hours at 4° C. The nitrocellulose was washed with blocking buffer and incubated with $^{125}$I-Protein A (0.4 mCi/ml) for 1–2 hours at room temp and exposed to X-ray film.

Radioiodination of PDGF BB. PDGF BB was iodinated by a modification of the Bolton-Hunter procedure described by Duan et al. (1991, *J. Biol. Chem.* 266:413–418, which is incorporated herein by reference). Briefly, $^{125}$I-diiodo Bolton-Hunter reagent (1 mCi) was dried under nitrogen. Then, PDGF BB (2.5 μg) was added to the $^{125}$I-diiodo Bolton-Hunter reagent in 10 μl of 0.1 M sodium borate (pH 8.5), for 15 min at 4° C. The reaction mixture was quenched with 500 μl of 0.1 M sodium borate, 0.2 M glycine, pH 8.5, for 10 min at 4° C. This material was subjected to gel filtration chromatography on a PD10 column previously equilibrated with 0.3 M acetic acid containing 1 mg/ml BSA. Peak radiolabelled protein fractions were detected using a gamma counter. Typically the specific activity of iodinated PDGF BB was 50000 counts/ng.

Binding of $^{125}$I-PDGF BB to intact HR5 cells. HR5 cells were harvested with PBS containing 2 mM EDTA for 20 min at 37° C. Washed HR5 cells (1×10$^6$ cells/100 μl) were incubated in triplicate in suspension with various concentrations of MAb (or F(ab')$_2$ or Fab fragments) in PBS containing 0.5% BSA for 30 min at room temp. HR5 cells were incubated with $^{125}$I-PDGF BB (approx. 1 ng/tube) in the absence (total binding) or presence (non-specific binding) of 100-fold excess unlabelled PDGF BB and carrier protein (platelet poor plasma, 50 μl) for 45 min at room temp. The final volume of the incubation was 500 μl. The incubation mixture (400 μl) was layered on Ficoll-paque (700 μl) and centrifuged. The supernatant was removed and the radioactivity in the cell pellet was determined.

Phosphorylation Assay. HR5 cells were grown to confluence in 6-well dishes and primary cells were cultured in 100 mm dishes. Cells were washed twice with cold serum-free DMEM, and incubated on ice for 10 min. Cells were preincubated in duplicate with MAb 2A1E2 for 30–45 min on ice on a rotary shaker, and then ligand PDGF BB was added to the wells and the incubation was continued for 1.5–2 hours. Cells were washed twice with cold PBS and solubilized in either Lysis Buffer (100 mM Tris, pH8, 30 mM sodium pyrophosphate, 50 mM sodium fluoride, 5 mM EDTA, 5 mM EGTA, 1% SDS, 100 mM DTT), or in IP buffer, both containing 1 mM PMSF and 1 µM sodium orthovanadate. Samples were then processed further prior to electrophoresis.

Mitogenesis in human foreskin fibroblast AG01523B cells and baboon smooth muscle cells. Human foreskin fibroblast AG01523B cells and baboon smooth muscle cells were gown to confluence in 96-well dishes. Baboon smooth muscle cells were quiesced by incubating overnight with DMEM containing 0.5% calf serum. Cells were then incubated in triplicate with various concentrations of MAb 2A1E2 in the presence of PDGF BB for 18 hours at 37° C., followed by 5 hours at 37° C. with 2 µCi/well of $^3$H-thymidine. Control baboon primary smooth muscle cells were incubated in parallel with a non-specific MAb and control AG01523B cells were incubated with a non-inhibitory anti-PDGF beta receptor Mab (4C5C8). Wells were then washed with ice-cold 5% TCA (2×250 µl), and solubilized with 0.25 N NaOH (2× 100 µl). The solubilized samples were transferred to scintillation vials and radioactivity was determined.

Dimerization Assay. Confluent HR5 cells were cultured as described above in 100 mm dishes. Cells were washed twice in cold PBS, and incubated with various concentrations of MAb 2A1E2 in PBS containing BSA (1.5 mg/ml) and 25 mM Hepes for 1 hour at 4° C. PDGF BB was added to the cells and the incubation was continued for 2 hours at 4° C. Cells were washed twice in cold PBS, and incubated for 30 min at 4° C. with cross-linker $BS^3$ (0.75 mg/plate) in PBS containing 25 mM Hepes. The reaction was terminated by dilution in quench buffer (0.025 M Tris, pH 7.4, containing 150 mM NaCl; 10 ml/plate). Cells were extracted for 20 min at 4° C. in IP buffer containing 1 mM PMSF and 100 µM sodium orthovanadate (0.5 ml/plate). Cell lysates were immunoprecipitated overnight at 4° C. using polyclonal anti-human beta receptor Ab (AB88, 1:500 dilution). Then, Protein A CL4B (60 µl of a 50% slurry) was added to each sample. After 1 hour at 4° C., beads were washed serially with PBS containing 0.5% NP40, 0.5 M lithium chloride containing 0.5% NP40, 0.5 M lithium chloride, and finally with water. Samples were solubilized with Laemnli sample solubilizing buffer, and subjected to SDS-polyacrylamide gel electrophoresis on a 3%–8% gradient gel, followed by Western transfer to nitrocellulose. Western blots were either incubated with antiphosphotyrosine MAb (1:1000), or with Ab88 (1:500 dilution) overnight at 4° C., followed by $^{125}$I-Protein A (0.15 µCi/ml) for 2 hours at room temp. Western blots were then exposed to X-ray film.

Results

Figure 2A:
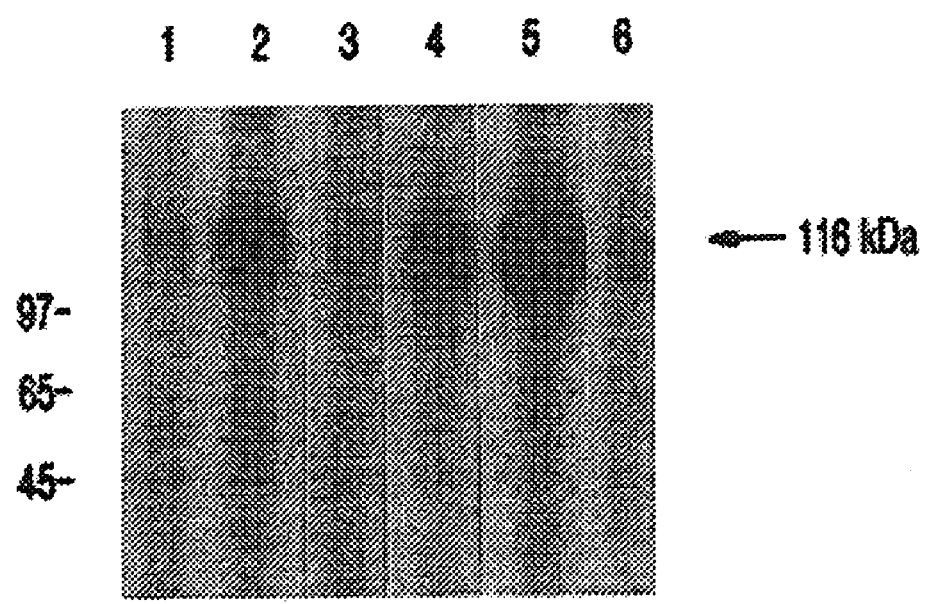
FIG. 2A. Western Blot of Secreted 5 Domain Extracellular PDGF Beta Receptor pΔ1-5. Reduced (Lanes 1–3) and non-reduced (Lanes 4–6) secreted extracellular domain of PDGF beta receptor (PΔ1-5, 5 μg/lane) was electrophoresed on 7% Laemmli gels, followed by Western transfer as described in Methods. The nitrocellulose was blocked in phosphate-buffered saline (PBS) containing 2% milk, cut into strips and incubated overnight at 4° C. with 60 μg/ml of either MAb 2A1E2 (Lanes 1 and 4), another PDGF beta receptor monoclonal antibody (1C7D5) (Lanes 2 and 5), or a non-specific monoclonal antibody (Lanes 3 and 6). The nitrocellulose strips were washed with PBS containing 0.5% milk and 0.1% Tween 20, incubated with $^{125}$I-labelled protein A for 2 hours at room temperature, and exposed to X-ray film. The arrow indicates the position of pΔ1-5.
Figure 2B:
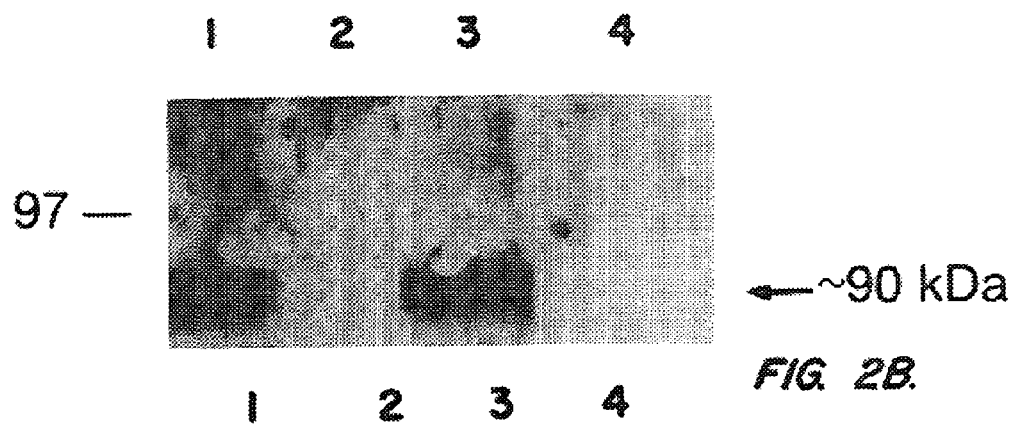
FIG. 2B. Immunoprecipitation of Secreted 4 Domain Extracellular PDGF Beta Receptor pΔ2-7. Secreted 4 domain extracellular PDGF beta receptor pΔ2-7 (2.6 μg) was incubated with either MAb 2A1E2 (Lane 2, 5 μg), 1C7D5 (Lane 3, 5 μg) or nonspecific MAb (Lane 4, 5 Mg) in a final volume of 500 μl in I.P. buffer for 3 hours at 4° C. Protein A sepharose CL4B: Protein G sepharose CL4B (1:1) was added to each tube (60 μl of 50% slurry) and the incubation was continued for 2 hours at 4° C. The beads were spun down, washed 5× in I.P. buffer and electrophoresed on a 10% Laemmli gel. The gel was transferred onto nitrocellulose and blocked in PBS containing 5% milk. The blot was incubated with a 1:100 dilution of a rabbit polyclonal anti-PDGF beta receptor Ab (1-3-5) in PBS containing 0.5% milk. After incubating overnight, the blot was washed, incubated with $^{125}$I-Protein A, washed, and exposed to X-ray film. Lane 1 shows a standard of PΔ2-7 without immunoprecipitation. The arrow indicates the position of pΔ2-7.
Figure 2C:
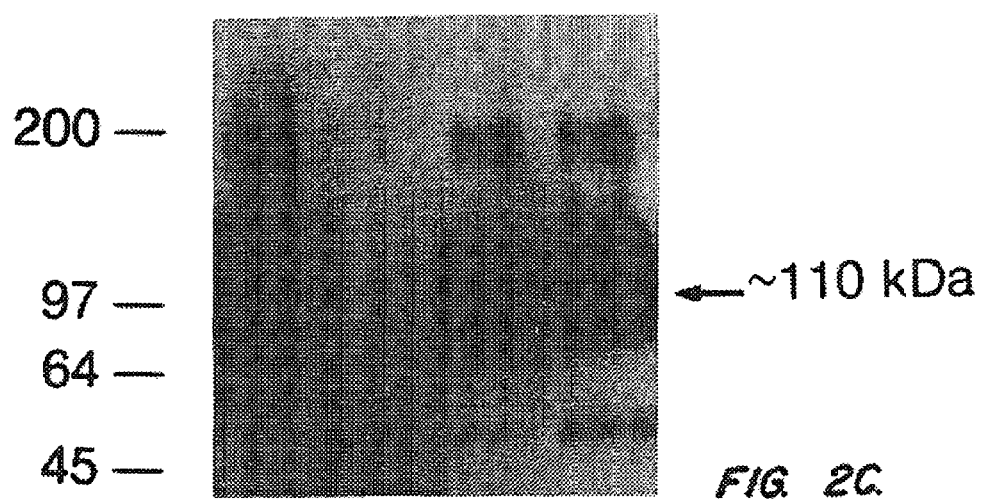
FIG. 2C. Immunoprecipitation of Secreted Extracellular PDGF Beta Receptor by MAb 2A1E2. Extracellular human PDGF beta receptor (pΔ1-5, 5 μg) was immunoprecipitated with 5 μg of either nonspecific MAb (Lane 2), MAb 2A1E2 (Lane 3), or 1C7D5 (Lane 4), as described for panel A. The samples were processed and the blot was incubated with rabbit polyclonal anti-PDGF beta receptor 1-3-5 (1:100 dilution) and $^{125}$I-protein A, as described in the legend for Panel B. Lane 1 contains 5 μg of standard pΔ1-5.

Properties of MAb 2A1E2. MAb 2A1E2 is an $IgG_1$ monoclonal antibody. Western analysis shows that MAb 2A1E2 recognizes non-reduced human PDGF beta receptor (FIG. 2, Panel A, Lane 4) but does not recognize reduced protein (FIG. 2, Panel A, Lane 1). MAb 2A1E2 immunoprecipitates full-length extracellular receptor (pΔ1-5; residues 1–499) from solution (FIG. 2, Panel C, Lane 3).

Figure 3B:
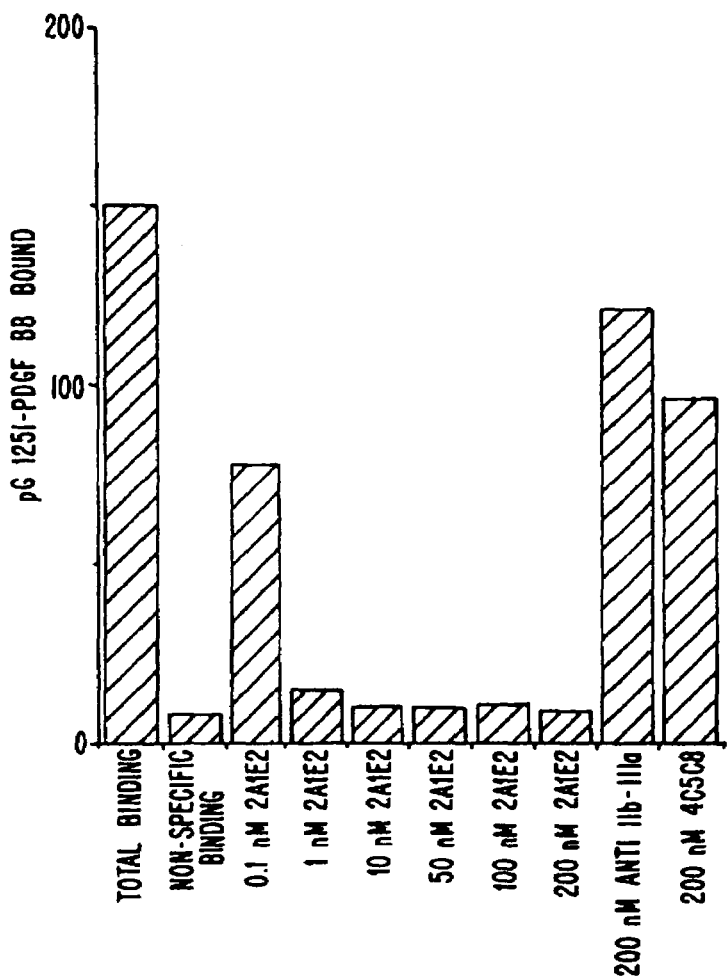
FIG. 3. Inhibition of $^{125}$I-PDGF BB Binding to HR5 Cells. A) HR5 cells were incubated with various concentrations of MAb 2A1E2 or control MAbs (200 nM anti-IIb/IIIa or 200 nM 4C5C8) as described in Methods. The cells were then incubated with $^{125}$I-PDGF BB and the bound radioactivity was determined as described. Non-specific binding is defined as the amount of $^{125}$I-PDGF BB bound in the presence of 100-fold excess unlabelled PDGF BB. B) HR5 cells were incubated with various concentrations of full-length MAb 2A1E2, MAb 2A1E2-F(ab')2, or MAb 2A1E2-Fab, and 100 nM full-length anti-IIb/IIIa as described in Methods. Total binding of $^{125}$I-PDGF BB to the cells in the presence and absence of MAbs and their derivatives was measured. The amount of $^{125}$I-PDGF BB bound in the presence of 100 fold-excess unlabelled PDGF BB represents non-specific binding.

Dose-dependent inhibition of $^{125}$I-PDGF BB binding to HR5 cells by MAb 2A1E2. When HR5 cells (CHO-K cells which express the full length human PDGF beta receptor) are incubated first with MAb 2A1E2 followed by $^{125}$I-PDGF BB, significant (48.1%) inhibition is observed at a concentration as low as 0.1 nM MAb, compared to cells not treated with MAb 2A1E2. When 1 nM or greater concentrations of MAb 2A1E2 are used, there is 100% inhibition of ligand binding to the full-length PDGF beta receptor on the cells (FIG. 3, Panel A). When 200 nM of a different, non-inhibitory MAb (4C5C5) to PDGF beta receptor is used in the preincubation, the amount of inhibition is only 36.1%. This is comparable to the effect of 200 nM of a non-relevant MAb (anti-IIb/IIIa) (19.18% inhibition). The amount of $^{125}$I-PDGF BB binding in the presence of 1 nM MAb 2A1E2 is equivalent to the amount of ligand binding seen in the presence of 1500-fold excess of unlabelled PDGF BB (FIG. 3, Panel A), or the amount of binding of ligand to non-transfected CHO cells that do not express a human PDGF receptor (data not shown).

To determine if the inhibition seen with MAb 2A1E2 was due to steric hindrance, we prepared $F(ab')_2$ and Fab fragments of the MAb. These proteolytic fragments of the antibody still recognized the PDGF beta receptor in ELISA (data not shown), though their activity was diminished slightly. When these were used in the radiolabelled ligand binding assay, we found that the antibody fragments still inhibited binding of $^{125}$I-PDGF BB to the full-length PDGF beta receptor on HR5 cells in a concentration-dependent manner (FIG. 3, Panel B). However, complete inhibition was seen with 10 nM MAb 2A1E2 $F(ab')_2$ or Fab fragments, whereas 1 nM intact antibody completely inhibited binding. Binding of ligand in the presence of 1 nM $F(ab')_2$ fragments was inhibited by 64.5%, and binding in the presence of 1 nM Fab fragments was inhibited by 50%.

Figure 4:
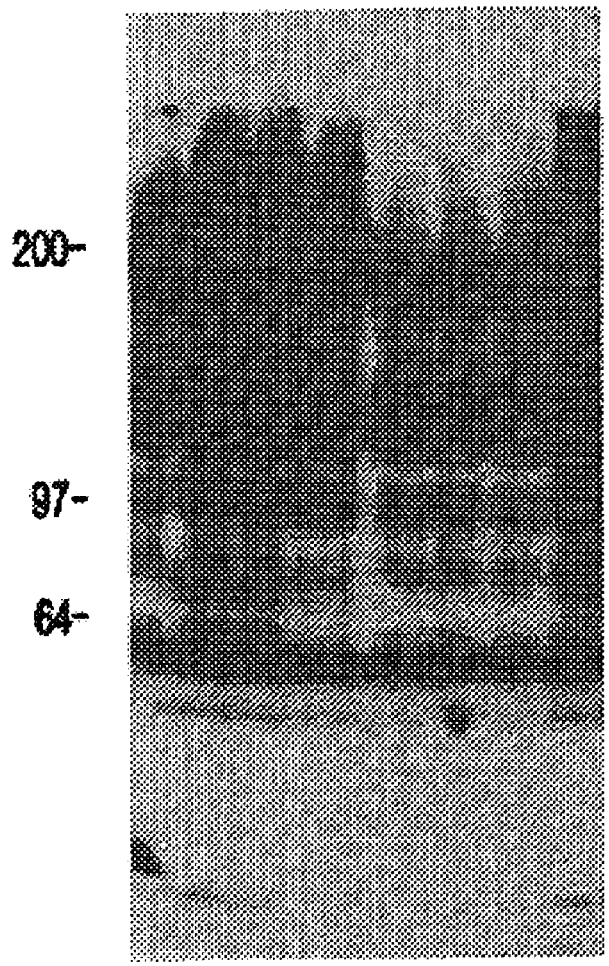
FIG. 4. Inhibition of Phosphorylation of HR5 cells by MAb 2A1E2. Confluent monolayers of HR5 cells in 6-well dishes were preincubated in duplicate with various MAbs, followed by incubation with ligand PDGF BB as described in Methods. Cells were solubilized, and the equivalent of one 6-well dish was electrophoresed on a 7% Laemmli gel and transferred onto nitrocellulose. The western blot was blocked and then incubated with antiphosphotyrosine MAb. The blot was then incubated with $^{125}$I-Protein A and autoradiographed. Lanes 3–7 represent wells which were preincubated with either 0.13 nM MAb 2A1E2 (Lane 3), 1.3 nM MAb 2A1E2 (Lane 4), 13.3 nM MAb 2A1E2 (Lane 5), 0.13 μM MAb 2A1E2 (Lane 6) or 0.53 AM MAb 2A1E2 (Lane 7), followed by 100 ng/ml PDGF BB. Lane 2 shows the degree of phosphorylation in the presence of 100 ng/ml PDGF BB, when the cells were first preincubated with 0.53 μM of a non-specific MAb, and Lane 8 shows PDGF BB-induced phosphorylation when cells are preincubated with 0.53 μM of PDGF beta receptor MAb 4C5C8. The arrow indicates the position of the full length human PDGF beta receptor.

Inhibition of Phosphorylation by MAb 2A1E2. As shown in FIG. 4, MAb 2A1E2 specifically inhibited PDGF induced phosphorylation in HR5 cells in a concentration-dependent manner, with approximately 50% inhibition occurring at a concentration of 1.3 nM (Lane 4) and 100% inhibition occurring at 13.3 nM MAb 2A1E2 (Lane 5). Control non-relevant MAb (anti-IIb/IIIa) had no effect (Lane 3) and MAb 4C5C8, which was also developed against the human PDGF beta receptor but recognizes a different epitope, had no effect on ligand-induced phosphorylation (Lane 8).

Figure 5:
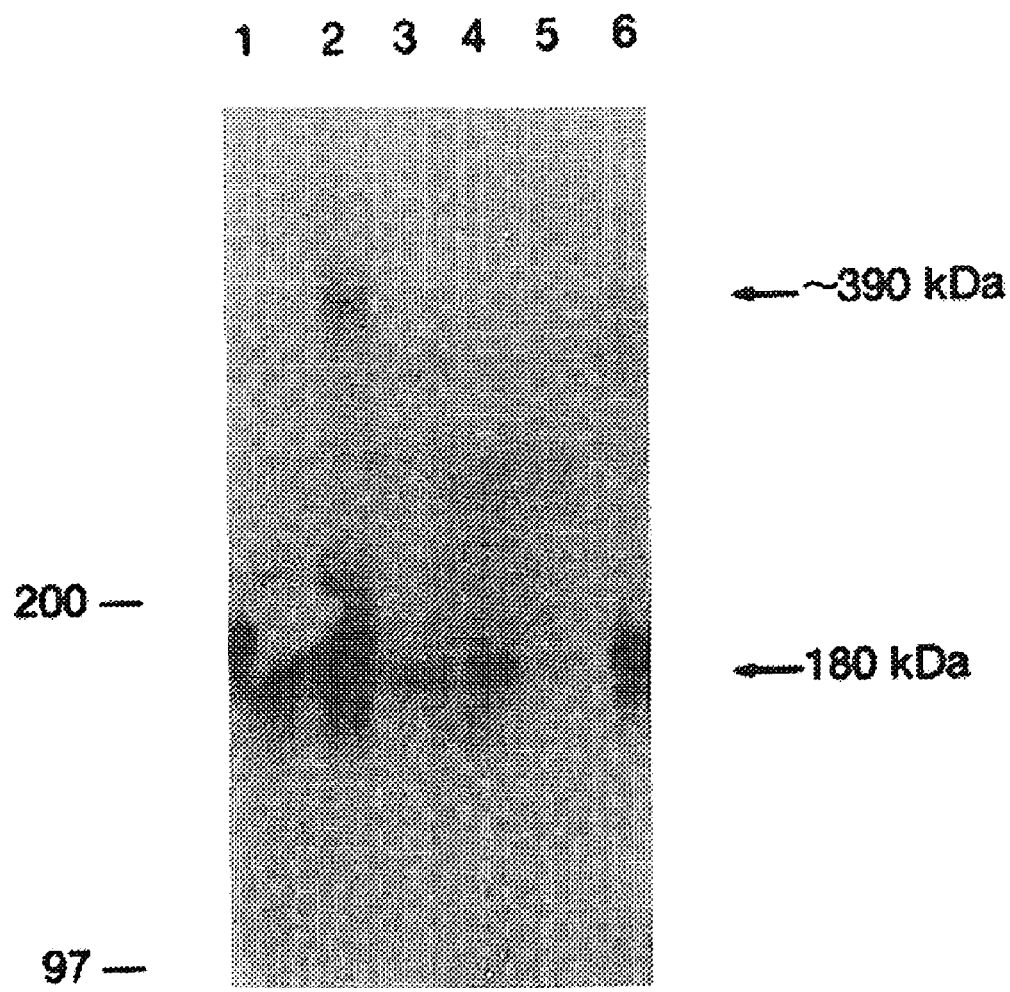
FIG. 5. Inhibition of PDGF BB-Mediated Dimerization of PDGF receptor by MAb 2A1E2. HR5 cells were incubated with either 13 nM MAb 2A1E2 (Lane 3), 0.13 μM MAb 2A1E2 (Lane 4), or 1.3 μM MAb 2A1E2 (Lane 5), followed by 100 ng/ml PDGF BB, and cross-linking was carried out as described in Methods. Lane 6 represents the effect of 0.1 μM anti-IIb/IIIa MAb on dimerization. Lane 1 shows the relative amount of dimer in the absence of added crosslinker and lane 2 shows the amount of dimerized PDGF receptor in the absence of antibody.

Effect of MAb 2A1E2 on PDGF BB Induced Dimerization of the Human PDGF beta Receptor. Treatment of HR5 cells with PDGF BB results in ligand-mediated phosphorylation (FIG. 5, 180 KDa protein in lanes 1–6) and dimerization (FIG. 5, 390 KDa protein in lanes 2 and 6) of the PDGF beta receptor. When HR5 cells are first preincubated with MAb 2A1E2 and then with PDGF BB, dimerization was inhibited at all the tested concentrations (FIG. 5, Lanes 3, 4 and 5). This data indicates that binding of MAb 2A1E2 on the receptor excludes ligand binding and receptor dimerization.

Figure 6:
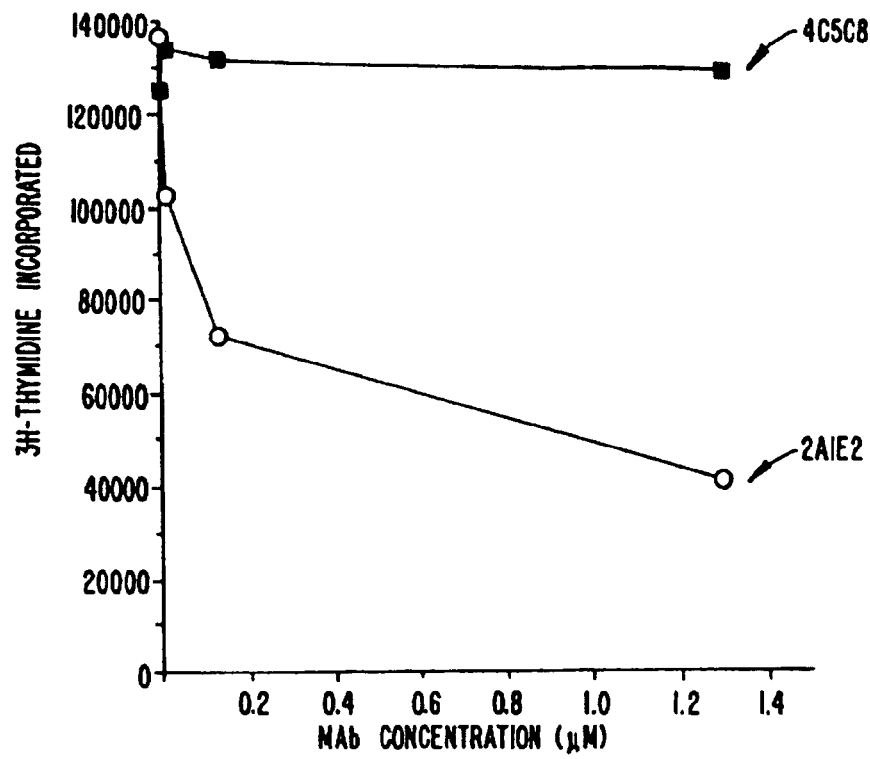
FIG. 6. Inhibition of Mitogenesis in AG01523B cells by MAb 2A1E2. Cells were grown to confluence and incubated as described in Methods with various concentrations of either MAb 2A1E2 (open circles) or non-inhibitory control PDGF beta receptor MAb 4C5C8 (solid squares) in the presence of 50 ng/ml of PDGF BB. $^{3}$H-thymidine incorporation was measured as described.

Inhibition of Mitogenesis by MAb 2A1E2. As shown in FIG. 6, MAb 2A1E2 inhibits PDGF BB-induced mitogenesis in human foreskin fibroblast AG01523B cells in a concentration-dependent manner, with maximum inhibition (69.55%) occurring at a concentration of 1.3 µM. When a non-inhibitory MAb, 4C5C8, was used, we did not detect significant inhibition of mitogenesis. Increasing the concentration of MAb 2A1E2 did not improve the degree of inhibition, primarily because these cells also express PDGF alpha receptor (data not shown) which is not bound or inhibited by 2A1E2.

Figure 7:
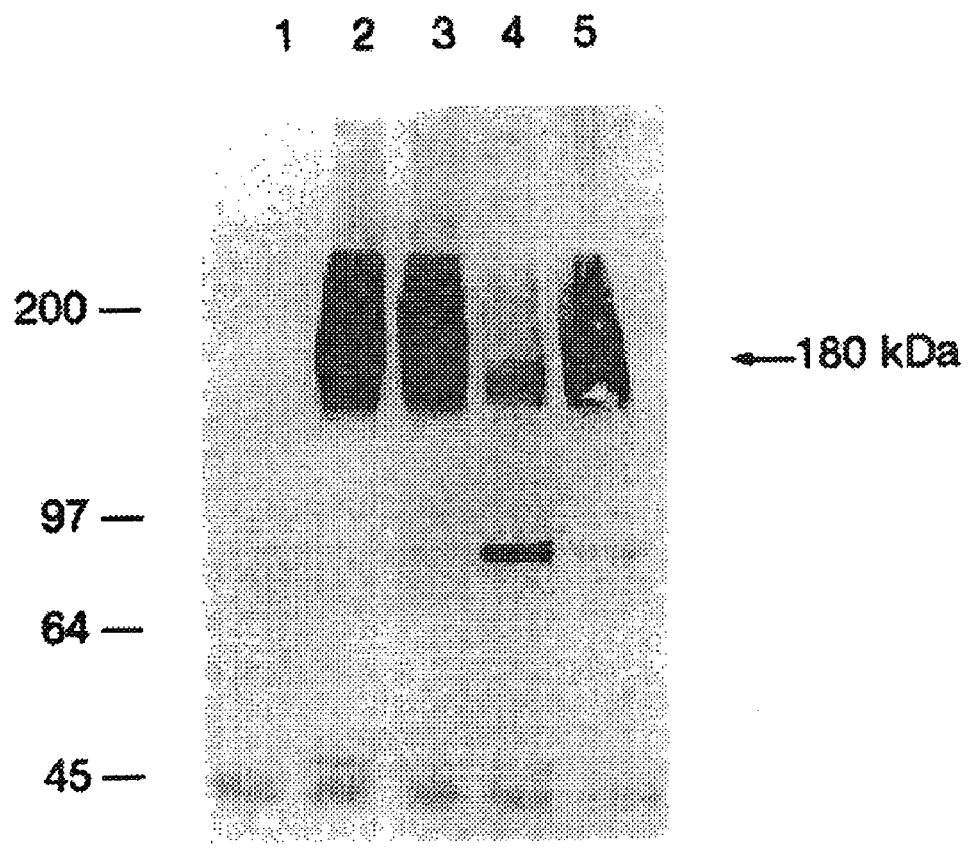
FIG. 7. Inhibition of Phosphorylation by MAb 2A1E2 in Baboon Smooth Muscle Cells. Baboon smooth muscle cells were incubated with no PDGF BB (Lane 1), or with 100 ng/mL PDGF BB in the absence of MAb (Lane 2), or in the presence of 2 nM MAb 2A1E2 (Lane 3), 200 nM MAb 2A1E2 (Lane 4) or 20 nM MAb 2A1E2 (Lane 5). Ligand induced phosphorylation was determined by Western analysis, as described in Methods.

We also determined the effect of various concentrations of MAb 2A1E2 on primary smooth muscle cells from baboon artery. PDGF BB-mediated PDGF receptor phosphorylation in baboon artery smooth muscle cells was inhibited by 200 nM and 20 nM MAb 2A1E2 (FIG. 7, Lanes 4 and 5, respectively).

Figure 8:
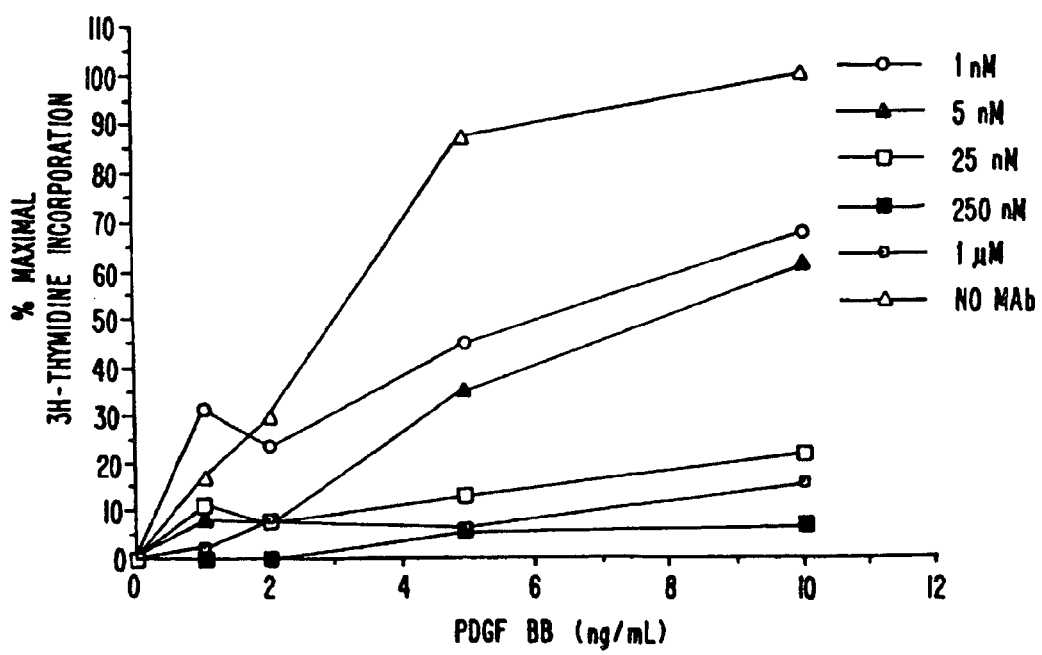
FIG. 8. Inhibition of Mitogenesis by MAb 2A1E2 in Baboon Smooth Muscle Cells. Confluent baboon smooth muscle cells were incubated with 1 nM, 5 nM, 25 nM, 250 nM, or 1 μM MAb 2A1E2 in the presence of various concentrations of PDGF BB. $^{3}$H-Thymidine incorporation was measured as described in Methods. Data is expressed as a percent of maximal $^{3}$H-thymidine incorporated (approximately 30–50000 cpm) at saturating ligand concentration (10 ng/ml) in the absence of MAb. $^{3}$H-Thymidine incorporation in the absence of PDGF BB is 5–8000 cpm. The graph represents the average of 4 separate experiments.

As seen in FIG. 8, 1 nM MAb 2A1E2 inhibits $^3$H-thymidine incorporation in the presence of 1–2 ng/ml of PDGF BB by 90%, and 25 nM MAb inhibits mitogenesis by 80% at ligand concentrations ranging from 1–10 ng/ml. Concentrations of MAb 2A1E2 greater than 250 nM inhibit mitogenesis by 90% at all tested concentrations of ligand. When non-relevant MAbs are used there is no significant effect on mitogenesis in baboon smooth muscle cells.

Figure 3A:
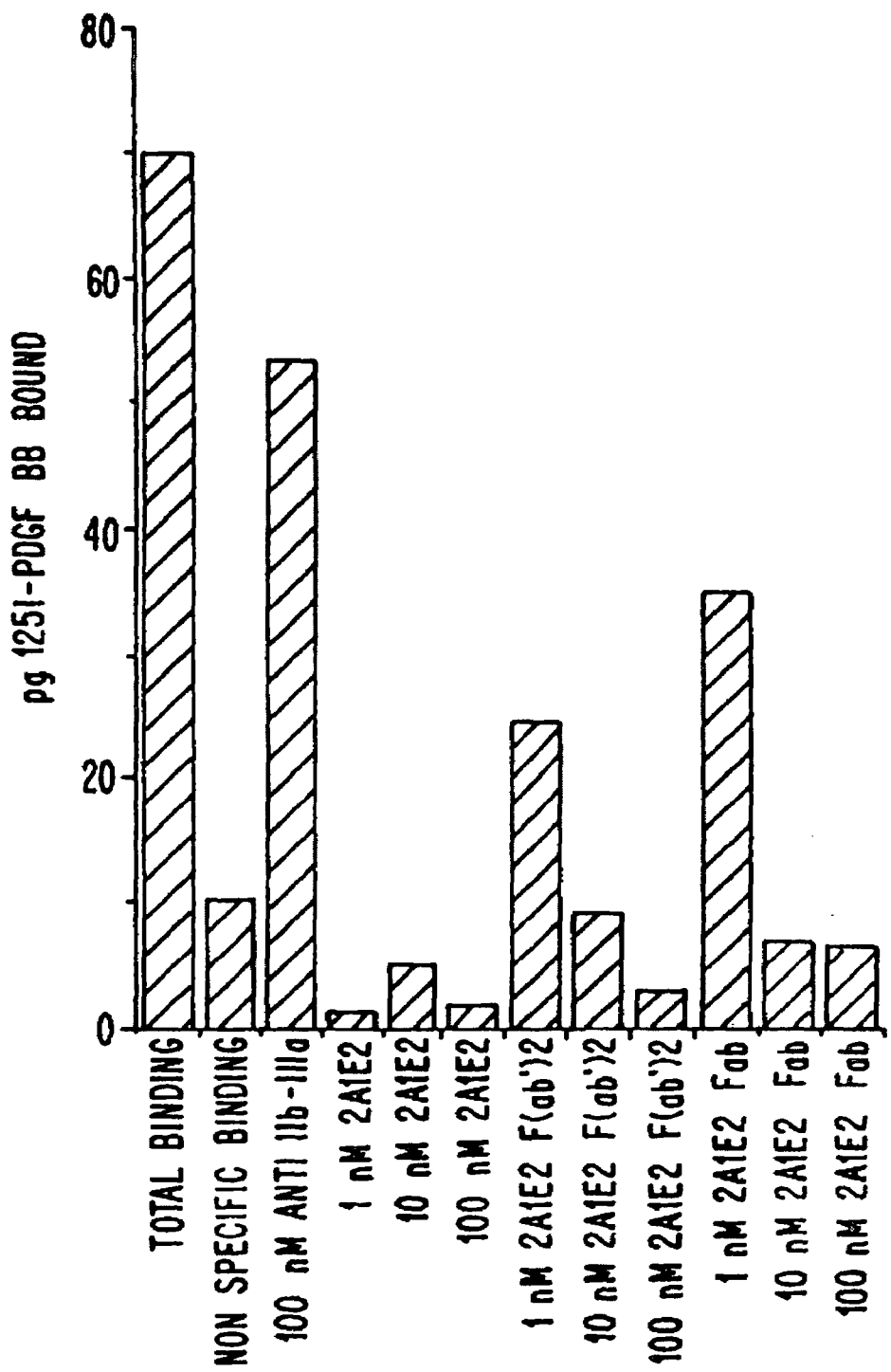

In summary, we have disclosed a monoclonal antibody, MAb 2A1E2, that is highly specific for the human PDGF beta receptor. MAb 2A1E2 inhibits the binding of PDGF to the human type beta PDGF receptor at nanomolar concentrations, and thus inhibits receptor activation as indicated by inhibition of ligand-mediated phosphorylation and dimerization. The antibody inhibits mitogenesis in vitro at micromolar concentrations. The proteolytic fragments of the MAb retain inhibitory function, as measured by the inhibition of $^{125}$I-PDGF BB binding (FIG. 3A). There is a specific and significant inhibition of ligand-induced autophosphorylation of the PDGF beta receptor (FIG. 4), at concentrations as low as 1.3 nM MAb 2A1E2. Consequently, we have found complete inhibition of PDGF induced mitogenesis in HR5 cells (data not shown) at 0.1 μM MAb 2A1E2, and in human foreskin fibroblast cells (AG01523B) 70% inhibition is achieved at 1 μM MAb 2A1E2 concentration.

MAb 2A1E2 was also tested for cross-reactivity with smooth muscle cells from baboon brachial artery. PDGF BB-induced phosphorylation (FIG. 7) and mitogenesis (FIG. 8) was inhibited up to 80% by 20–25 nM MAb 2A1E2. Monoclonal antibody 2A1E2 does not cross-react with PDGF receptors from dog, rat, mouse, or pig, and also does not cross-react with human type alpha PDGF receptor (data not shown).

EXAMPLE 2

Materials and Methods

Construction and Expression of Beta Platelet Derived Growth Factor Receptor (β-PDGFR) cDNA Variants A human β-PDGFR cDNA encoding only the extracellular region of the receptor due to the introduction of a translational stop signal at codon 530 has been cloned into the mammalian expression vector pBJ-1 to give the construct designated pBJpΔ1 (Fretto et al. JBC 268:3625, 1993). Starting with pBJpΔ1, additional stop codons were introduced such that each variant encoded a β-PDGFR extracellular domain with a progressively larger truncation at its carboxy terminus. These mutants designated pBJpΔ2, pBJpΔ3, pBJpΔ4 and pBJpΔ5 contain a translational stop signal at codon 415, 314, 214 and 124 respectively. In order to generate an additional series of β-PDGFR cDNA constructs which encode extracellular domains with progressively larger truncations at the amino terminus, deletions were introduced into pBJpΔ1. These deletions were done such that codon 34 was fused to the internal codon 124, 214, 315 or 416 resulting in mutants designated pBJpΔ6, pBJpΔ7, pBJpΔ8 and pBJpΔ9 respectively. All DNA manipulations were done following standard procedures (Maniatis et al. Molecular Cloning C.S.H. Laboratory, NY 1982). Site directed mutagenesis was performed using the method of Kunkel (Kunkel et al. Methods in Enzymol., 154:367, 1987) and each construct was verified by dideoxy chain termination DNA sequencing (Sanger et al., Proc. Natl. Sci. USA, 74:5463, 1977).

The constructs pBJpΔ1 through 9 were each transiently expressed in COS-7 cells using standard methods (Maniatis et al. Molecular Cloning C.S.H. Laboratory, NY 1982). Each of the mutant β-PDGFR extracellular domains was secreted by the transfected cells and collected in the conditioned media for further analysis.

Western Blot Analysis of β-PDGFR Extracellular Domain Proteins

Conditioned media containing approximately 10 ng of each of the β-PDGFR mutant proteins were subjected to 4–20% SDS-PAGE (Laemmli, et al. L. Mol. Biol. 80:575, 1973) and Western Blot analysis was done using a rabbit polyclonal antibody (Ab 3981) or monoclonal antibody 2A1E2 each of which were raised against purified full length β-PDGFR extracellular domain protein (Fretto et al. JBC 268:3625, 1993, Ramakrishnan et al. Growth Factors, 8:253, 1993, Harlow, et al., Antibodies, C.S.H. NY, 1988, polyclonal antibody provided by Jim Tomlinson of COR Therapeutics).

Development of ELISA for Analysis of β-PDGFR Extracellular Domain Proteins

A sandwich ELISA was developed for analysis of β-PDGFR extracellular domain proteins (Harlow, et al., Antibodies, C.S.H. NY, 1988). Briefly, 0.2 mg of polyclonal Ab 3981 directed against the full length β-PDGFR extracellular domain was immobilized in wells of 96 well plates and the wells were washed followed by blocking with 0.2% Tween 20. Varying amounts of conditioned media containing each of the β-PDGFR extracellular domain proteins were then incubated at 37 degrees for 1 hour in wells containing the immobilized Ab 3981. In order to estimate their concentrations in the conditioned media, the captured β-PDGFR proteins were then detected by incubation with biotinylated Ab 3981 (0.35 mg/ml), excess antibody was washed out and incubation was continued with a 1:2000 dilution of avidin-peroxidase (Boehringer Mannheim). Wells were washed again and peroxidase substrate (ABTS™) was added; product formation was monitored at 650 nM using a plate reader (Molecular Devices). A standard curve was generated using known amounts of highly purified full length β-PDGFR extracellular domain (Fretto et al. JBC 268:3625, 1993).

PDGF BB Solid Phase Binding Assay

PDGF receptor binding assays were performed as described previously with some minor modifications (Fretto et al. JBC 268:3625, 1993). Briefly, β-PDGFR extracellular domain proteins were immobilized in wells of 96 well plates by capturing them with Ab 3981 which had been directly immobilized on plastic as described above. After removing unbound receptor, each well was incubated with increasing amounts of PDGF BB (0.13–100 ng/ml), excess ligand was washed out and bound ligand was detected with anti-PDGF goat polyclonal antibody as previously described (Fretto et al. JBC 268:3625, 1993).

Results

Structural Analysis of β-PDGFR Mutant Proteins

Figure 9:
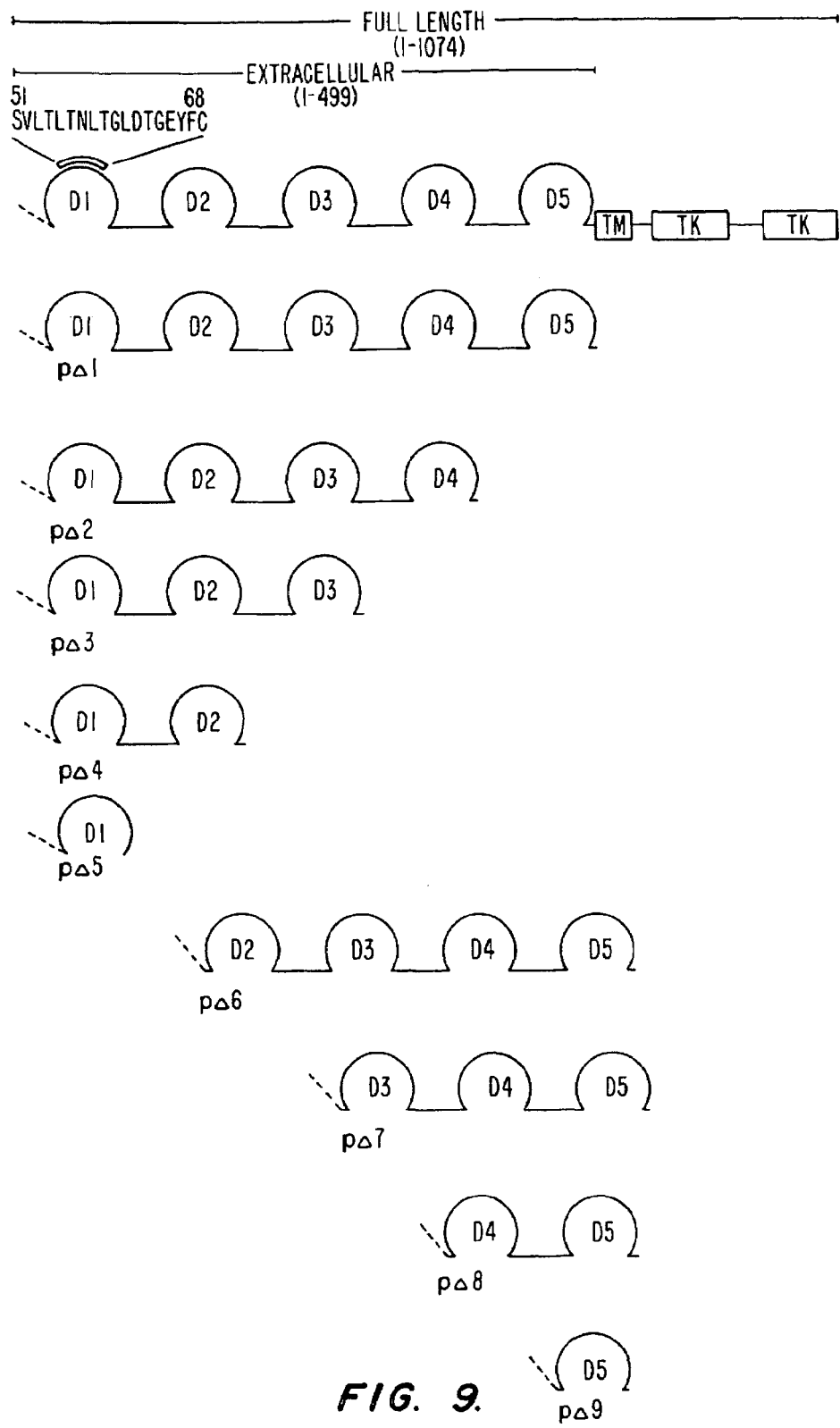
FIG. 9. Structure of the β-PDGFR full length protein and the deletion mutant proteins, pΔ1-9. This figure indicates the immunoglobulin-like domains (D1-5) within the extracellular region as described by Williams (Science 243:1564, 1989), TM is transmembrane domain, TK is tyrosine kinase domain. The dotted line represents the receptor signal sequence required for transport through the cellular secretory pathway that is encoded by codons 1–34. pΔ1-9 represent a series of mutant proteins.
Figure 10:
FIG. 10. Western Blot analysis of β-PDGFR mutant proteins, pΔ1-9, using polyclonal Ab 3981. Approximately 10 ng of each mutant protein pΔ1 (lane 1), pΔ2 (lane 2), pΔ3 (lane 3), pΔ4 (lane 4), pΔ5 (lane 5), pΔ6 (lane 6), pΔ7 (lane 7), pΔ8 (lane 8) and pΔ9 (lane 9) were separated on 4–20% SDS-PAGE and immunoblotted with Ab 3981.

The β-PDGFR extracellular region is composed of 5 immunoglobulin-like domains (D1–D5) based on the spacing of its cysteine residues and on amino acid sequence similarities to known immunoglobulin molecules (Williams, Science 243:1564, 1989). As depicted in FIG. 9, a series of mutant β-PDGFR cDNAs have been constructed that encode either the full length extracellular region (pBJpΔ1) or they encode proteins with progressively larger deletions that increase in size by one domain at a time starting at the carboxy terminus (pBJpΔ2 through 5) or at the amino terminus (pBJpΔ6 through 9). To verify that each of these mutant cDNA was directing the synthesis of a β-PDGFR extracellular domain protein with the expected molecular weight, Western Blot analysis was performed. As shown in FIG. 10, each of the mutant β-PDGFR proteins encoded by pBJpΔ1-9, designated pΔ1-9, were readily detected. The largest receptor protein containing the entire extracellular region, pΔ1, migrated at about 100 kd as previously reported (Fretto et al. JBC 268:3625, 1993). Each of the other mutant proteins, pΔ2-9, were proportionately smaller than pΔ1 and their estimated molecular weights corresponded to that predicted from their cDNA sequences (FIG. 10).

Identification of Epitopes Recognized by β-PDGFR Blocking Monoclonal Antibody 2A1E2

Figure 11:
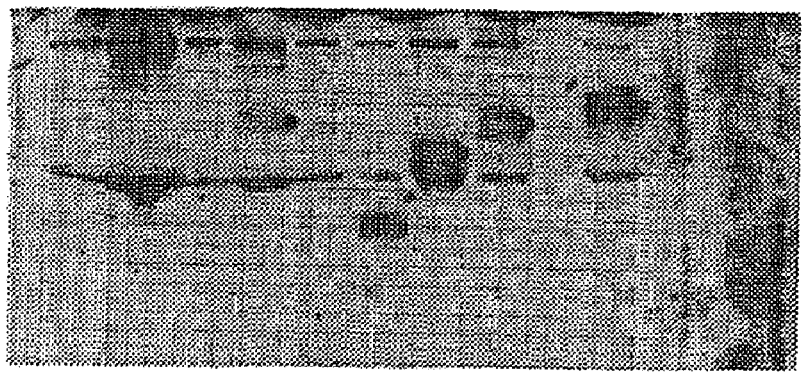
FIG. 11. Western Blot analysis of β-PDGFR mutant proteins, pΔ1-9, using monoclonal antibody 2A1E2.

The monoclonal antibody 2A1E2 potentially blocks a number of β-PDGFR functions including PDGF BB binding, receptor phosphorylation and PDGF mediated signal transduction (Ramakrishnan et al. Growth Factors, 8:253, 1993). This antibody was raised against the β-PDGFR protein containing the entire extracellular region, pΔ1, but the individual immunoglobulin-like domains (D1–D5) that are recognized by 2A1E2 are unknown. Because this antibody blocks receptor function, i.e., ligand binding, receptor phosphorylation and mitogenesis, identification of the immunoglobulin-like domains recognized by it should facilitate the identification regions important for receptor function. To identify the Δ-PDGFR immunoglobulin-like domain(s) recognized by 2A1E2, each of the mutant proteins was subjected to Western Blot analysis using 2A1E2 as the blotting antibody. As shown in FIG. 11, pΔ1, pΔ2, pΔ3, pΔ4 and pΔ6 proteins are all readily detected demonstrating that immunoglobulin-like domains D1, D3, D4 and D5 are not required for 2A1E2 recognition. D2 is the only immunoglobulin-like domain required for detection by 2A1E2 as demonstrated by the fact that each mutant receptor protein which lacks D2 (pΔ5, pΔ7, pΔ8 and pΔ9) is not detected (FIG. 11) although each of these mutant proteins are readily detected by the polyclonal antibody, Ab 3981, under similar conditions (FIG. 10). These data have been confirmed using ELISA analysis (data not shown). We conclude from these results that 2A1E2 recognizes epitopes within D2 of the β-PDGFR extracellular region.

Figure 12:
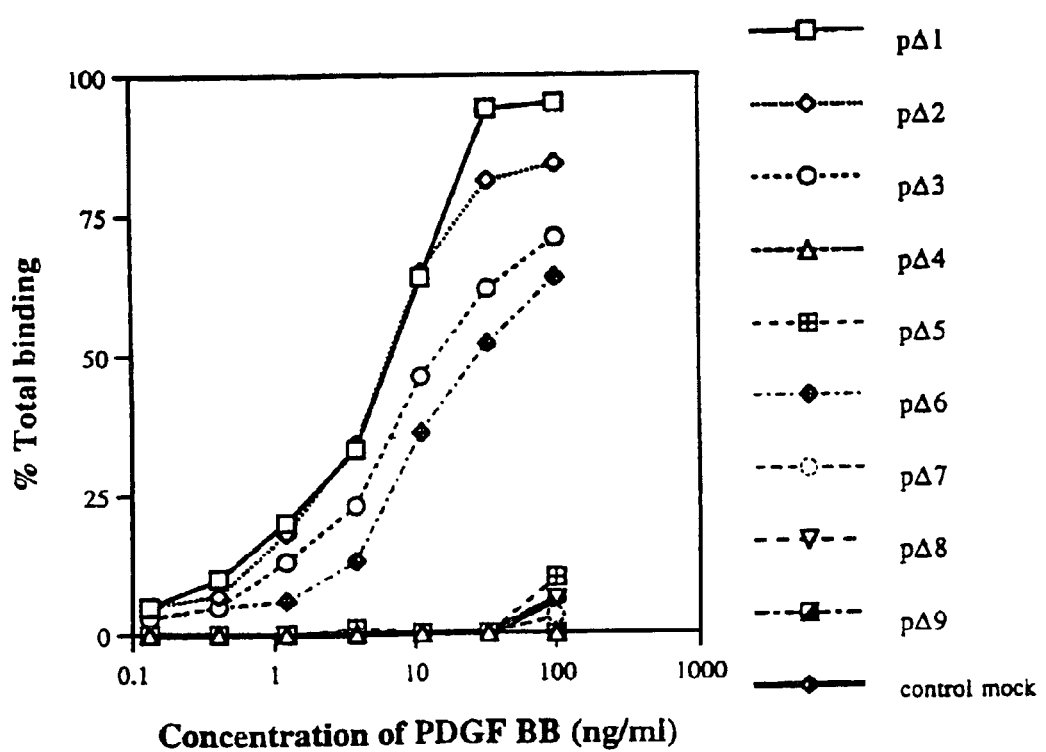
FIG. 12. Detection of PDGF BB binding to β-PDGFR mutant proteins, pΔ1-9. Each of the mutant proteins were immobilized in wells of 96 well dishes followed by incubation with PDGF BB at varying concentrations (0.13–100 ng/ml) and receptor bound ligand was detected with anti-PDGF polyclonal antibody.

Identification of Immunoglobulin-like Domains Within the β-PDGFR Extracellular Region Required for PDGF BB Binding Purified β-PDGFR full length extracellular domain protein, pΔ1, has been shown to bind PDGF BB with a kD value of 0.5 nM indicating that this truncated protein is highly active with respect to ligand binding (Fretto et al. JBC 268:3625, 1993). Therefore, evaluation of mutant proteins pΔ2-9 under similar conditions should allow for the identification of the immunoglobulin-like domains that are required for PDGF BB binding. This was done using a solid phase binding assay in which mutant β-PDGFR proteins are first immobilized and then the level of PDGF BB binding is determined as previously described (Fretto et al. JBC 268: 3625, 1993 and Materials and Methods). As shown in FIG. 12, PDGF BB binding to pΔ1, pΔ2, pΔ3 and pΔ6 was readily detected demonstrating that D1, D4 and D5 were not required for ligand binding. Furthermore, no detectable binding was observed when mutants lacking D2 and/or D3 (pΔ4, 5 and 7–9) were analyzed. These results demonstrate that the binding site for PDGF BB is within D2 and D3 of the β-PDGFR. Since 2A1E2 binds to D2, its neutralizing activity may result because of a direct interaction of this antibody with the ligand binding site of the β-PDGFR.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

What is claimed is:

1. A method of treating a PDGF-mediated disease involving proliferation, migration or chemotaxis of smooth muscle cells, comprising the administration of a therapeutically effective dose of an anti-platelet derived growth factor (PDGF) beta receptor antibody.

2. A method of inhibiting intimal hyperplasia in the vasculature of a mammal, comprising:
    administering to said mammal a therapeutically effective dose of an anti-platelet derived growth factor (PDGF) beta receptor antibody.

3. A method according to claim 2, wherein said antibody inhibits one or more intimal hyperplastic processes selected from the group consisting of vascular smooth muscle cell proliferation and vascular smooth muscle cell migration.

4. A method according to claim 2, wherein said antibody inhibits binding of PDGF to PDGF beta receptors.

5. A method according to claim 2, wherein said antibody is a monoclonal antibody.

6. A method according to claim 2, wherein said antibody is administered concurrently with, or within a therapeutically effective time period before an occurrence of acute vascular injury.

7. A method according to claim 6, wherein said injury is due to angioplasty, atherectomy or other invasive methods of plaque removal.

8. A method according to claim 2, wherein said antibody is administered within a therapeutically effective time period following an occurrence of acute vascular injury.

9. A method according to claim 8, wherein said injury is due to angioplasty, atherectomy or other invasive methods of plaque removal.

10. A method according to claim 2, wherein said antibody is administered concurrently with, or within a therapeutically effective time period before, emplacement of a vascular graft or transplanted organ.

11. A method according to claim 2, wherein said antibody is administered within a therapeutically effective time period following emplacement of a vascular graft or transplanted organ.

12. A method according to claim 2, wherein one or more anti-PDGF beta receptor antibodies is administered to said mammal.

13. A method according to claim 2, wherein said antibody is a humanized monoclonal antibody.

14. A method according to claim 2, wherein said antibody is a single chain antibody.

15. A method according to claim 2, wherein said antibody is a chimeric antibody.

16. A method according to claim 15, wherein said antibody is a human-mouse chimeric antibody.

17. A method according to claim 16, wherein said chimeric antibody comprises mouse variable domains operably linked to human constant domains.

18. A method of inhibiting coronary restenosis in a mammal, comprising the step of:
    administering to said mammal a therapeutically effective dose of a humanized anti-platelet derived growth factor (PDGF) beta receptor antibody before an occurrence of vascular injury.

19. A method according to claim 18, wherein said injury is due to angioplasty, atherectomy or other invasive methods of plaque removal.

* * * * *